United States Patent
Sandoval Rodríguez et al.

(10) Patent No.: US 12,227,537 B2
(45) Date of Patent: Feb. 18, 2025

(54) INTERMEDIATES FOR THE PREPARATION OF 11-METHYLENE STEROIDS

(71) Applicant: CRYSTAL PHARMA, S.A.U., Boecillo-Valladolid (ES)

(72) Inventors: Celso Miguel Sandoval Rodríguez, Boecillo-Valladolid (ES); Ignacio Herráiz Sierra, Boecillo-Valladolid (ES); Ivano Messina, Boecillo-Valladolid (ES); Jesús Miguel Iglesias Retuerto, Boecillo-Valladolid (ES)

(73) Assignee: CRYSTAL PHARMA, S.A.U., Boecillo-Valladolid (ES)

( * ) Notice: Subject to any disclaimer, the term of this patent is extended or adjusted under 35 U.S.C. 154(b) by 916 days.

(21) Appl. No.: 17/319,545

(22) Filed: May 13, 2021

(65) Prior Publication Data

US 2021/0269474 A1  Sep. 2, 2021

Related U.S. Application Data

(62) Division of application No. 16/081,835, filed as application No. PCT/EP2017/054952 on Mar. 2, 2017, now Pat. No. 11,034,716.

(30) Foreign Application Priority Data

Mar. 3, 2016 (EP) ..................... 16382092

(51) Int. Cl.
| | |
|---|---|
| C07J 11/00 | (2006.01) |
| C07J 1/00 | (2006.01) |
| C07J 21/00 | (2006.01) |
| C07J 33/00 | (2006.01) |
| C07J 43/00 | (2006.01) |
| C07J 51/00 | (2006.01) |

(52) U.S. Cl.
CPC .............. *C07J 11/00* (2013.01); *C07J 1/0059* (2013.01); *C07J 1/0096* (2013.01); *C07J 21/008* (2013.01); *C07J 33/007* (2013.01); *C07J 43/003* (2013.01); *C07J 51/00* (2013.01); *C07J 1/007* (2013.01); *C07J 1/0077* (2013.01); *C07J 1/0085* (2013.01)

(58) Field of Classification Search
CPC ........ C07J 1/0059; C07J 1/0096; C07J 11/00; C07J 1/0085; C07J 33/007; C07J 43/003; C07J 51/00

See application file for complete search history.

(56) References Cited

U.S. PATENT DOCUMENTS 3,927,046 A  12/1975  Van Den Broek

FOREIGN PATENT DOCUMENTS

| | | | |
|---|---|---|---|
| CN | 1865276 A | | 11/2006 |
| CN | 101440112 A | | 5/2009 |
| CN | 102964418 A | | 3/2013 |
| CN | 105906680 A | | 8/2016 |
| DE | 2 361 120 | | 6/1974 |
| IT | 2006MI0474 | * | 6/2006 |
| IT | 102006901396142 | | 9/2007 |
| WO | WO 2004/014934 | | 2/2004 |
| WO | WO 2013/071210 A1 | | 5/2013 |
| WO | WO 2013/135744 A1 | | 9/2013 |
| WO | WO 2014/037873 A1 | | 3/2014 |

OTHER PUBLICATIONS

Akhrem (Total Synthesis of Steroids, 1970, Plenum Press, New York, N .Y pp. i-362. (Year: 1970).
Chemical Abstracts Database AN: 2009:654414 (corresponding to CN 101440112 A).
Chemical Abstracts Database AN:2016:1419480 (corresponding to CN 105906680 A).
Corey et al. J. Am. Chem. Soc. 1999, vol. 121(4), 710-714.
Etonogesterol (Wikipedia, recovered from https://en.wikipedia.org/wiki/Etonogestrel on Nov. 12, 2019, pp. 1-8) (Year: 2019).
Gao et al. Steroids 1997, 62(5), 398-402.
Gao et al. Organic Preparation and Procedure Int., 1997, 29(5), 572-576.
Heuvel, M.J., et al. Recueil des Travaux Chimiques des Pays-Bas 1988, vol. 107, No. 4, p. 331-334.
International Search Report and Written Opinion, mailed Apr. 24, 2017, in International Application No. PCT/EP2017/054952.
Ringold et al., Tetrahedron 1958, 2(1-2), 164-165.
Van den Broek et al., J. Royal Nether. Chem. Soc. 1975, 94(2), 35-39.
Zaragoza Dorwald, Side Reactions in Organic Synthesis, 2005, WILEY-VCH Verlag GmbH & Co. KGaA, Weinheim, Preface. p. IX. (Year: 2005).
Zderic et al., J. Am. Chem. Soc. 1960, 82(13), 3404-3409.

* cited by examiner

*Primary Examiner* — Barbara P Badio
(74) *Attorney, Agent, or Firm* — Knobbe, Martens, Olson & Bear, LLP

(57) ABSTRACT

Compounds having the formula

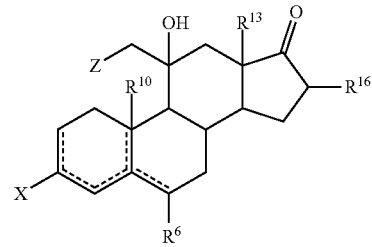

or solvates of the compounds can be used as intermediates in the preparation of the synthetic steroids, Etonogestrel and Desogestrel, as well as other pharmaceutically active agents.

4 Claims, No Drawings

INTERMEDIATES FOR THE PREPARATION OF 11-METHYLENE STEROIDS

PRIORITY AND CROSS REFERENCE TO RELATED APPLICATIONS

This application is a Divisional Application of U.S. patent application Ser. No. 16/081,835, filed Aug. 31, 2018, which is the U.S. National Phase Application under 35 U.S.C. § 371 of International Application No. PCT/EP2017/054952, filed Mar. 2, 2017, designating the U.S. and published in English as WO 2017/149091 A1 on Sep. 8, 2017, which claims the benefit of European Application No. EP 16382092.1, filed Mar. 3, 2016. Any and all applications for which a foreign or a domestic priority is claimed is/are identified in the Application Data Sheet filed herewith and is/are hereby incorporated by reference in their entirety under 37 C.F.R. § 1.57.

FIELD

The invention relates to a process for the selective olefination of 11,17-di-keto steroids to the corresponding 11-methylene-17-keto steroids, which are useful intermediates in the preparation of several pharmaceutically active agents, such as Etonogestrel and Desogestrel.

BACKGROUND

Desogestrel and Etonogestrel are synthetic steroids with strong progestational activity. They are used in third-generation contraceptive formulations.

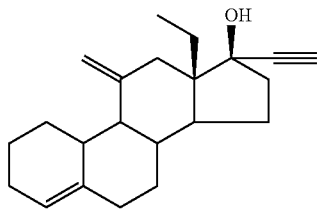

Desogestrel

Etonogestrel

Desogestrel is currently used as a synthetic progestin in numerous oral contraceptive formulations, whereas Etonogestrel is being used as synthetic progestin in the vaginal ring delivery system NuvaRing® and in the implant Implanon®.

Several synthetic methods have been described in the literature for the synthesis of these progestin compounds.

Desogestrel and Etonogestrel were described for the first time in the German patent DE 2361120 (also published as U.S. Pat. No. 3,927,046) which discloses the synthesis of Desogestrel. The synthesis of Desogestrel disclosed in U.S. Pat. No. 3,927,046, as well as in Heuvel, M. J., et al. Recueil des Travaux Chimiques des Pays-Bas 1988, vol. 107, no. 4, p. 331-334, employs the compound of formula (IV) as a key intermediate. This compound is obtained by olefination of the ketone in position 11 of compound (II), where the ketone groups at positions 3 and 17 are protected as ketals, followed by cleavage of the protecting groups in compound (III).

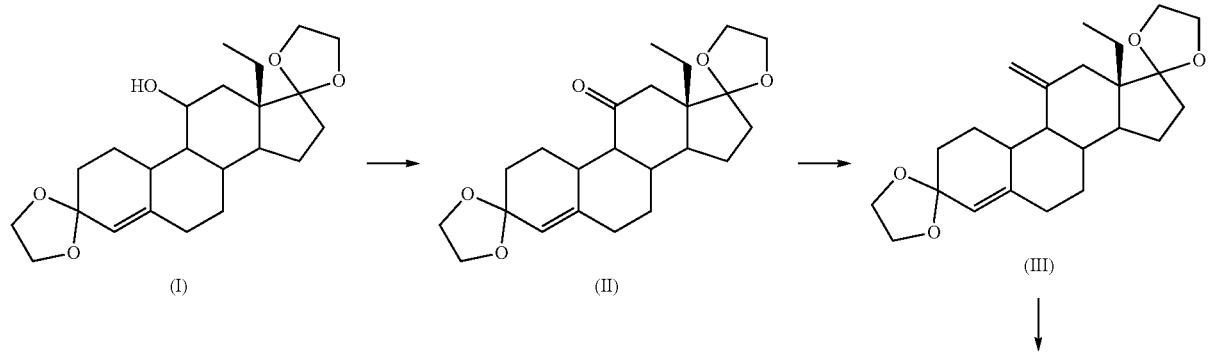

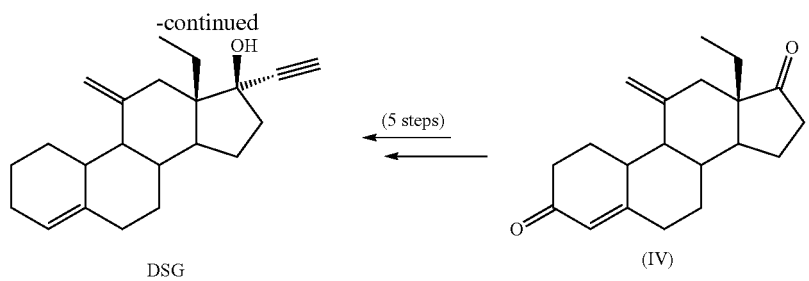

WO2004/014934 discloses the synthesis of desogestrel from 11α-hydroxy-18-methyl-estra-4-en-3,17-dione, which is obtained by microbiological hydroxylation in position 11a. Before creating the exo-methylene functionality in position 11, the ketone group at position 17 is protected.

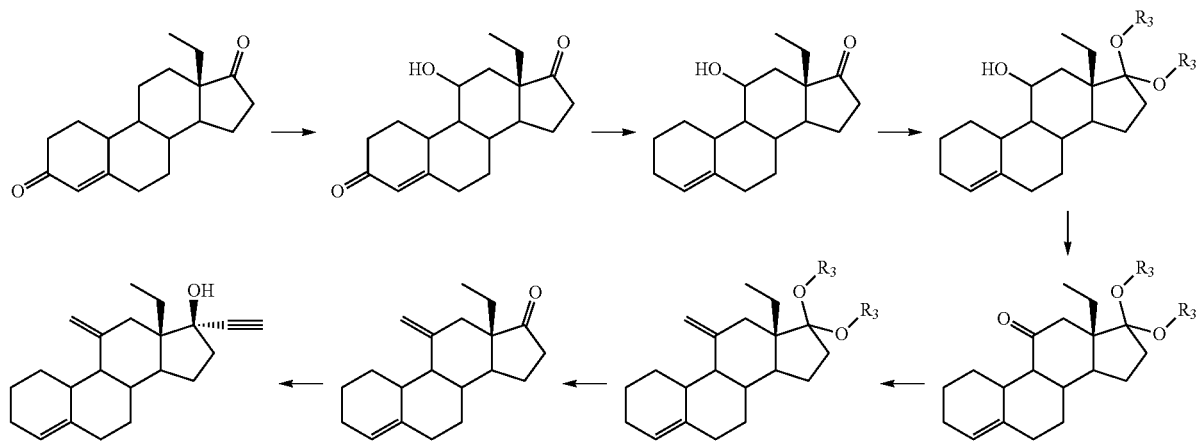

Desogestrel and etonogestrel can also be synthesised according to the method described in CN1865276 A. 11-oxo functionality is obtained by epoxide rearrangement and Birch reduction to afford the compound of formula (I). Olefination at position 11 of intermediate (II) affords the compound of formula (III), which is used as key intermediate for the preparation of both desogestrel and etonogestrel.

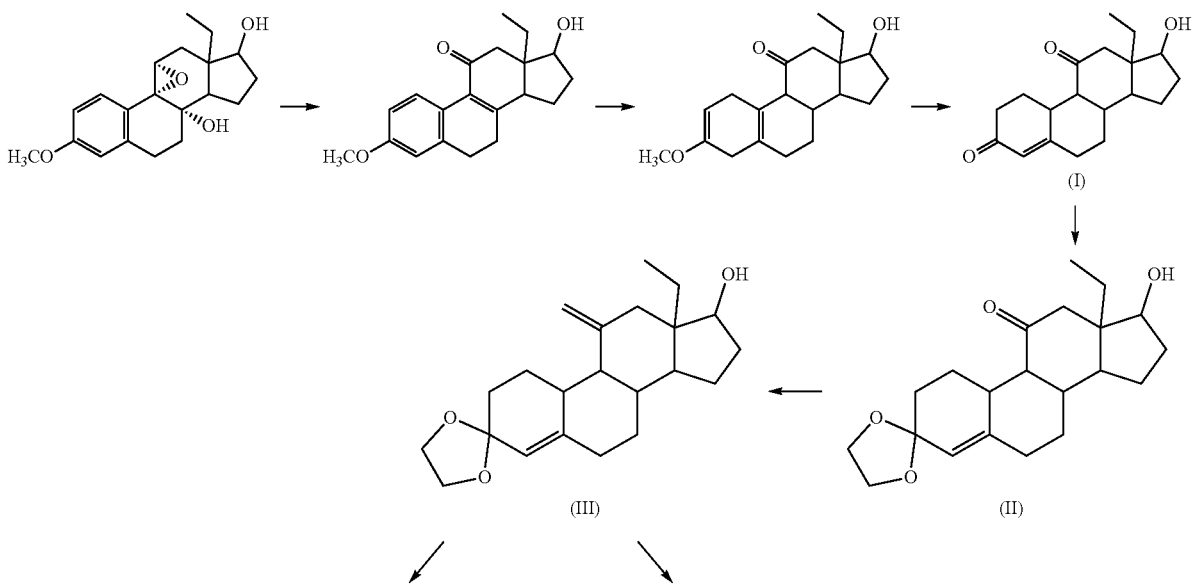

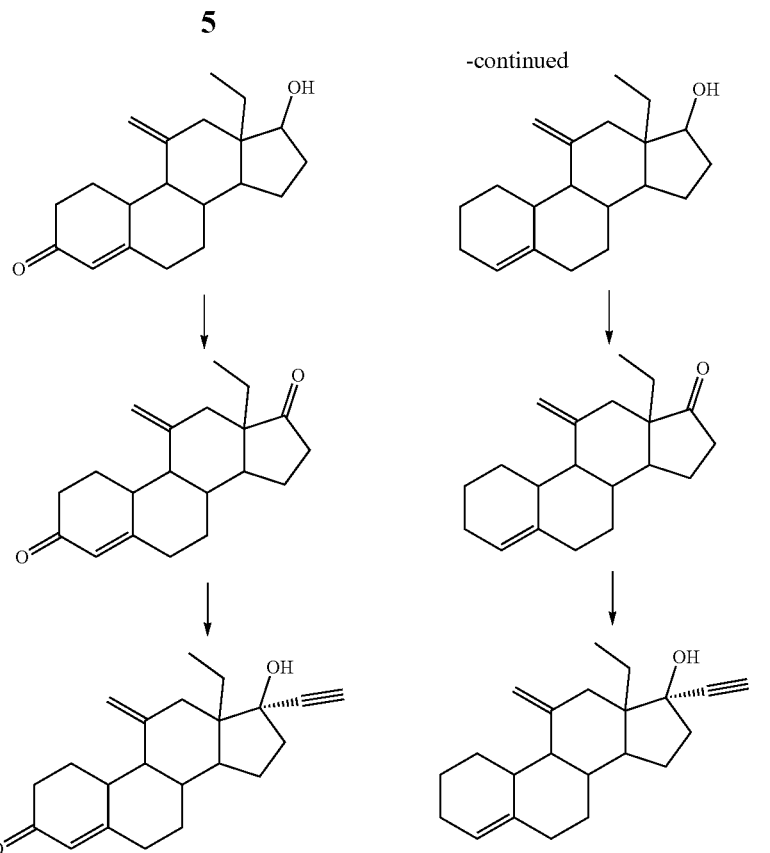
In order to generate the methylene group at position 11, addition of methyl lithium to the 11-keto group was performed over an intermediate compound substituted at position 17 with a hydroxyl protected group in the synthesis of etonogestrel disclosed by Gao et al in Steroids 1997, 62(5), 398-402.
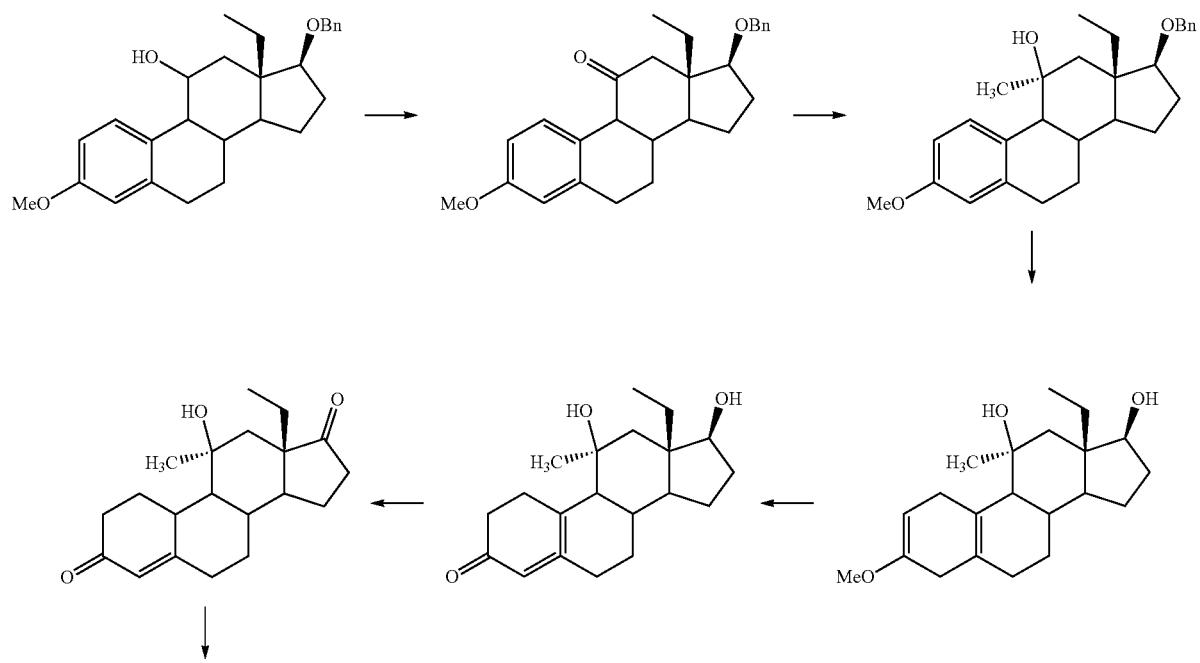

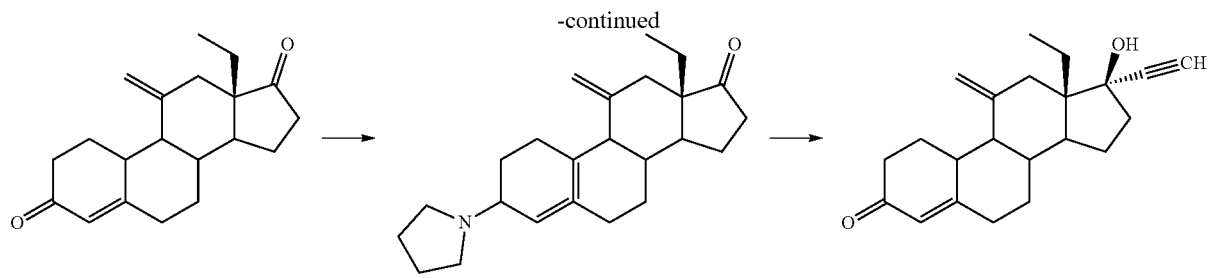

In Organic Preparation and Procedure Int., 1997, 29(5), 572-576, Gao et al described the synthesis of desogestrel from 13β-ethyl-11-hydroxy-gon-4-ene-3,17-dione. Again, olefination of the ketone at position 11 is performed after protection of the ketone groups at positions 3 and 17 as diethylene ketal.

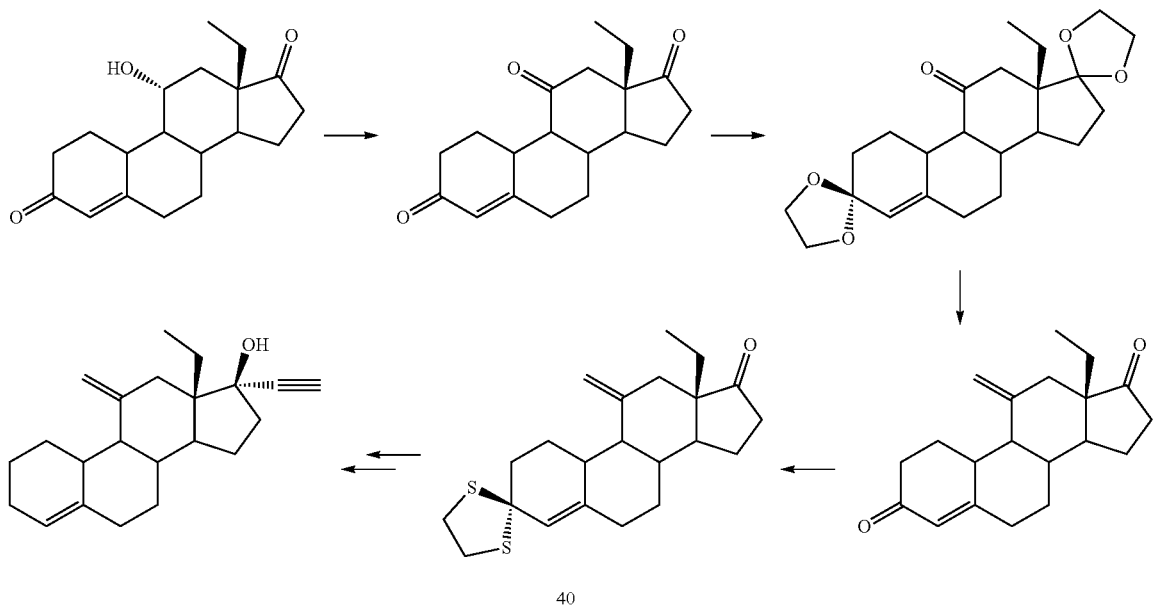

In CN102964418, selective protection of the 3-ketone of 13-ethyl-3,11,17-trione (I) as dithioketal followed by protection of the 17-carbonyl group in (III) as ketal afforded intermediates (V) and (XIII). Olefination at position 11 of said protected intermediates, deprotection of the dioxolane, ethynylation at position 17 and thioketal deprotection afforded etonogestrel.

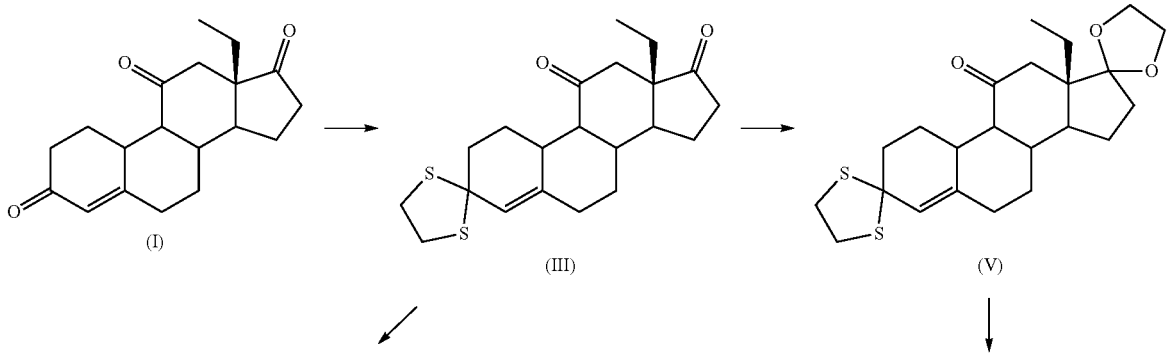

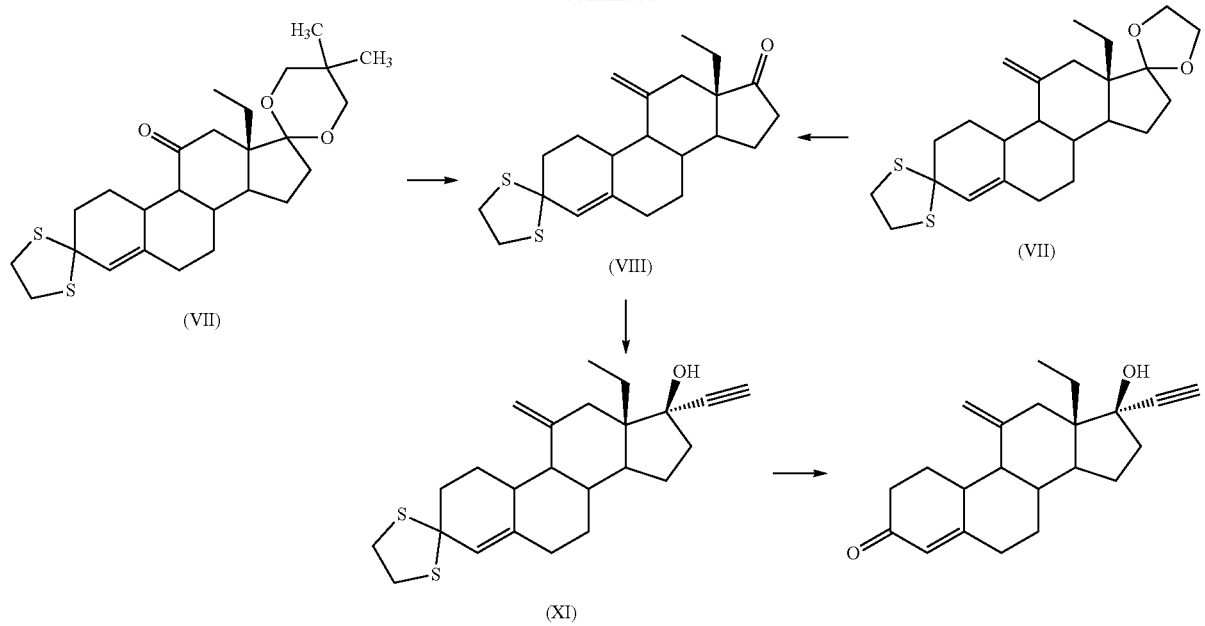
A similar strategy, selective protection of the ketone at position 3 as dithioketal, followed by protection of the 17-keto group with ethylene glycol, was also used in WO 2013/135744. The 11-methylene derivative (VII) was obtained through Wittig reaction or Peterson olefination. Subsequent alkynylation and deprotection gave rise to etonogestrel.
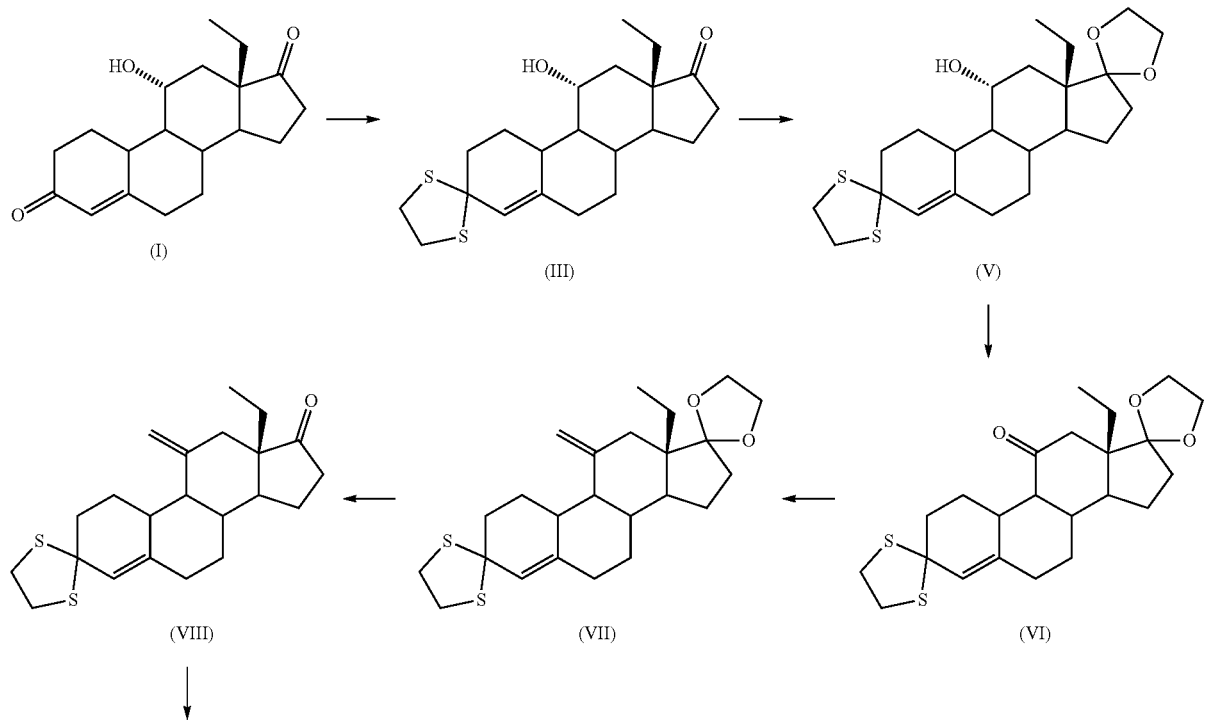

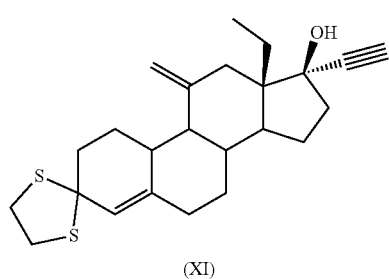

(XI)

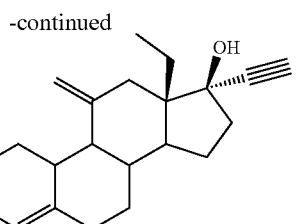

WO2013/071210 describes the synthesis of compound 9, a key intermediate to desogestrel and etonogestrel. Oxidation of alcohol 5 under Swern conditions yielded ketone 6, which was treated under Peterson olefination conditions. Birch reduction of triene 7 gave rise to diene 8, which was hydrolyzed to furnish 11-methylene diketone derivative 9. Again, protection of the 17 ketone was performed prior to olefination at position 11.

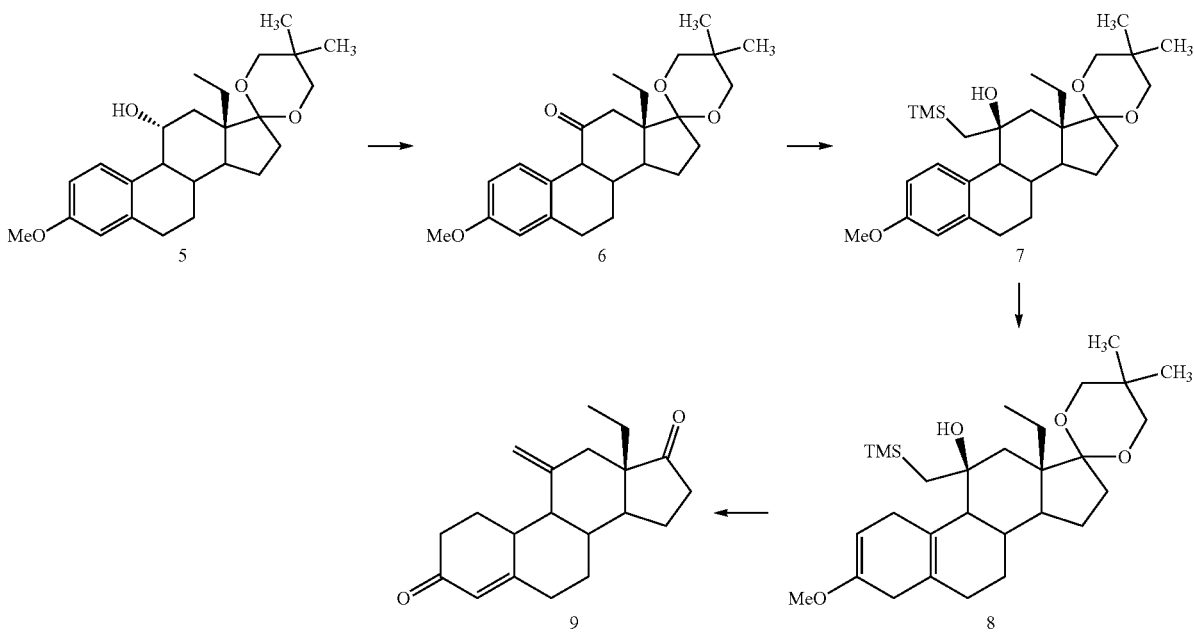

This same key intermediate to desogestrel and etonogestrel was also prepared in WO2014/037873. In this case, instead of protecting the 17-keto group before carrying out the olefination of the ketone at position 11, it was reduced to the corresponding hydroxyl compound (V) and then reoxidized to the ketone after the 11-methylene group was introduced.

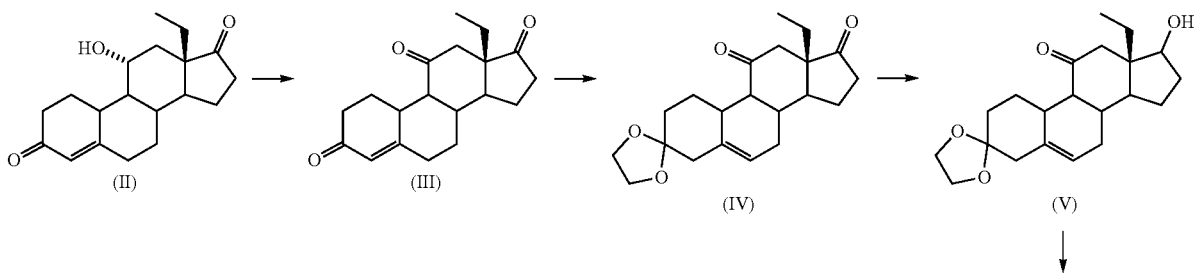

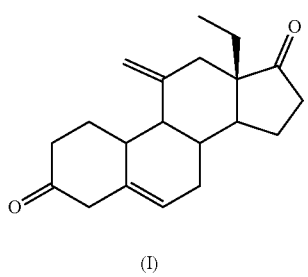

(I)

-continued

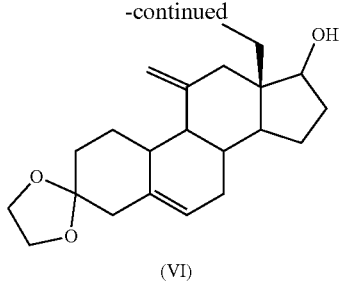

(VI)

(VI)

A totally different synthesis of desogestrel was disclosed by Corey et al. in J. Am. Chem. Soc. 1999, vol. 121(4), 710-714, where the steroid backbone was constructed. This strategy does not seem industrially applicable; at least 13 synthetic steps are required to obtain 17α-hydroxy-11-methylene-18-methylestr-4-en-3-one.

In summary, the methods disclosed in the prior art for the preparation of etonogestrel and desogestrel are too long and/or not industrially applicable. In general, most of the syntheses disclosed comprise olefination of the keto group at position 11. However, in all these methods additional steps of protection/deprotection or reduction/oxidation of the 17-keto group are required, which increases the number of steps of the synthesis.

It is therefore necessary to develop a new process for obtaining key intermediates in the synthesis of steroids such as desogestrel or etonogestrel which overcome all or part of the problems associated with the known processes belonging to the state of the art.

SUMMARY

The invention faces the problem of providing an improved process for the preparation of 11-methylene-17-keto compounds and derivatives thereof. In particular, the inventors have surprisingly found that 11,17-di-keto steroids can be selectively olefinated through reaction with a compound of formula (III) as defined herein. This olefination reaction is commercially important since the resulting 11-methylene-17-keto steroids are intermediates in the preparation of therapeutically valuable compounds, such as e.g. Etonogestrel and Desogestrel.

In addition, the process developed by the inventors allows preparing 11-methylene steroids in an efficient manner, using easily available starting materials and applying reaction conditions suitable for large scale production.

Thus, in a first aspect, the invention is directed to a process for the preparation of a compound of formula (I), or a solvate thereof

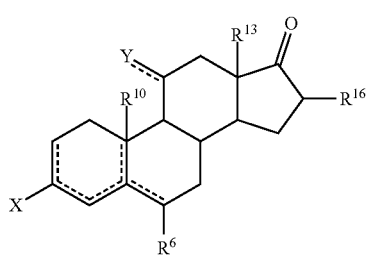

(I)

wherein

X represents H or it forms together with the carbon atom to which it is bonded a ketone protecting group;

Y together with the carbon atom to which it is bonded represents $C{=}CH_2$ or $C(OH)CH_2Z$, wherein Z is selected from H and $SiR'_3$ wherein each R' is independently selected from $C_1$-$C_6$ alkyl and $C_6$-$C_{10}$ aryl;

$R^6$ is selected from H, $C_1$-$C_6$ alkyl and halogen;

$R^{10}$ is selected from H, $C_1$-$C_6$ alkyl and halogen, or is absent when there is a double bond between $C_1$ and $C_{10}$;

$R^{13}$ is selected from H and $C_1$-$C_6$ alkyl;

$R^{16}$ is selected from H, $C_1$-$C_6$ alkyl and halogen; and

═ is a single or double bond;

which comprises reacting a compound of formula (II) or a solvate thereof

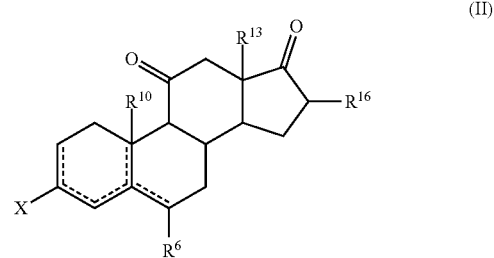

(II)

wherein X, $R^6$, $R^{10}$, $R^{13}$, $R^{16}$, and ═ can take the meanings defined above; with a compound of formula (III)

$$M\diagdown Z \qquad\qquad (III)$$

wherein Z can take the meanings defined above and M is selected from Li, MgBr, MgCl and MgI.

In another aspect, the invention is directed to an intermediate compound of formula (Ic), or a solvate thereof

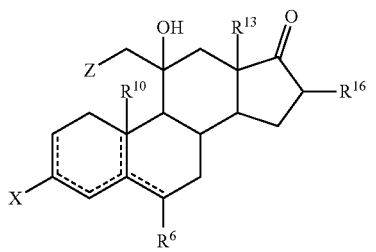

(Ic)

wherein
- X represents H or it forms together with the carbon atom to which it is bonded a ketone protecting group;
- Z is selected from H and SiR'$_3$ wherein each R' is independently selected from $C_1$-$C_6$ alkyl and $C_6$-$C_{10}$ aryl;
- $R^6$ is selected from H, $C_1$-$C_6$ alkyl and halogen;
- $R^{10}$ is selected from H, $C_1$-$C_6$ alkyl and halogen, or is absent when there is a double bond between $C_1$ and $C_{10}$;
- $R^{13}$ is selected from H and $C_1$-$C_6$ alkyl;
- $R^{16}$ is selected from H, $C_1$-$C_6$ alkyl and halogen; and
- ⹀ is a single or double bond.

In a further aspect, the invention is directed to an intermediate compound of formula (IVc), or a solvate thereof

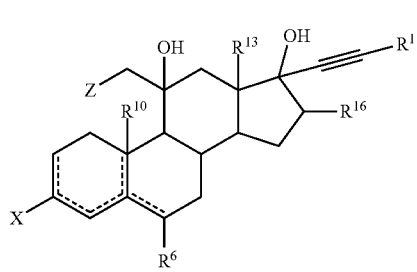

(IVc)

wherein
- X represents H or it forms together with the carbon atom to which it is bonded a ketone group or a ketone protecting group;
- Z is selected from H and SiR'$_3$ wherein each R' is independently selected from $C_1$-$C_6$ alkyl and $C_6$-$C_{10}$ aryl;
- $R^1$ is selected from H and SiR"$_3$, wherein each R" is independently selected from $C_1$-$C_6$ alkyl, $C_6$-$C_{10}$ aryl and halogen;
- $R^6$ is selected from H, $C_1$-$C_6$ alkyl and halogen;
- $R^{10}$ is selected from H, $C_1$-$C_6$ alkyl and halogen, or is absent when there is a double bond between $C_1$ and $C_{10}$;
- $R^{13}$ is selected from H and $C_1$-$C_6$ alkyl;
- $R^{16}$ is selected from H, $C_1$-$C_6$ alkyl and halogen; and
- ⹀ is a single or double bond.

DETAILED DESCRIPTION

The term "alkyl" refers to a linear or branched alkane derivative containing from 1 to 6 ("$C_1$-$C_6$ alkyl"), preferably from 1 to 3 ("$C_1$-$C_3$ alkyl"), carbon atoms and which is bound to the rest of the molecule through a single bond. Illustrative examples of alkyl groups include methyl, ethyl, n-propyl, i-propyl, n-butyl, i-butyl, t-butyl, pentyl, hexyl.

The term "aryl" refers to an aromatic group having between 6 and 10, preferably 6 or 10 carbon atoms, comprising 1 or 2 aromatic nuclei bound through a carbon-carbon bond or fused to one another. Illustrative examples of aryl groups include phenyl, naphthyl, diphenyl, indenyl, phenanthryl, etc.

The term "halogen" refers to bromine, chlorine, iodine or fluorine.

The term "cycloalkyl" refers to a radical derived from cycloalkane containing from 3 to 7 ("$C_3$-$C_7$ cycloalkyl"), preferably from 3 to 6 ("$C_3$-$C_6$ cycloalkyl") carbon atoms. Illustrative examples of cycloalkyl groups include cyclopropyl, cyclobutyl, cyclopentyl, cyclohexyl, etc.

"Heterocyclyl" refers to a stable cyclic radical of 3 to 10 members, preferably a cycle of 5 or 6 members consisting of carbon atoms and from 1 to 5, preferably from 1 to 3, heteroatoms selected from nitrogen, oxygen and sulfur, and which may be completely or partially saturated or be aromatic ("heteroaryl"). In the present invention, the heterocyclyl can be a mono-, bi- or tricyclic system which may include fused ring systems. Illustrative examples of heterocyclyl groups include, for example, pyrrolidine, piperidine, piperazine, morpholine, tetrahydrofuran, benzimidazole, benzothiazole, furan, pyrrole, pyridine, pyrimidine, thiazole, thiophene, imidazole, indole, etc.

The term "ketone protecting group", as used herein, refers to a group blocking the ketone function for subsequent reactions that can be removed under controlled conditions. The use of ketone-protecting groups is well known in the art for protecting groups against undesirable reaction during a synthetic procedure and such protecting groups are known (e.g. T. H. Greene and P. G. M Wuts, Protective Groups in Organic Synthesis, 4$^{th}$ edition, John Wiley & Sons, 2007). Virtually any ketone protecting group can be used to put the invention into practice. Illustrative, non-limiting examples of ketone protecting groups include:

acyclic ketals, dithioketals and hemithioketals

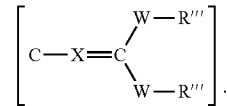

W can be oxygen or sulfur, and each R'" can be independently selected from $C_1$-$C_6$ alkyl and benzyl. Examples of acyclic ketals and dithioketals include dimethyl ketal, diethyl ketal, diisopropyl ketal, dibutyl ketal, dibenzyl ketal, dimethyl thioketal, diethyl thioketal, diisopropyl thioketal, dibutyl thioketal, dibenzyl thioketal;

cyclic ketals, dithioketals and hemithioketals

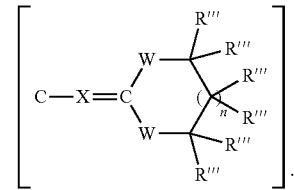

W can be oxygen or sulfur, n can be 0, 1 or 2, and each R'" can be independently selected from H and $C_1$-$C_6$ alkyl. Examples of cyclic ketals, dithioketals and hemithioketals include 1,3-dioxolane, 4-methyl-1,3-dioxolane, 4,5-dimethyl-1,3-dioxolane, 4,4,5,5-tetramethyl-1,3-dioxolane, 1,3- dioxane, 4-methyl-1,3-dioxane, 5-methyl-1,3-dioxane, 4,4-dimethyl-1,3-dioxane, 5,5-dimethyl-1,3-dioxane, 4,5-dimethyl-1,3-dioxane, 4,6-dimethyl-1,3-dioxane, 1,3-dioxapane, 1,3-dithiolane, 1,3-dithiane, 1,3-oxathiolane;
enol ethers

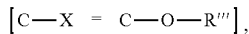

in which case there would additionally be a double bond between $C_2$ and $C_3$ or between $C_3$ and $C_4$. R''' can be selected from $C_1$-$C_6$ alkyl and benzyl. Examples of enol ethers include methyl enol ether, ethyl enol ether, propyl enol ether, butyl enol ether, benzyl enol ether;
enamines

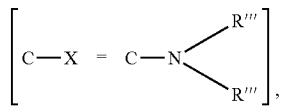

in which case there would additionally be a double bond between $C_2$ and $C_3$ or between $C_3$ and $C_4$. Each R''' can be independently selected from $C_1$-$C_6$ alkyl and benzyl, or the two R''' groups together with the nitrogen atom to which they are bonded form a 5- or 6-membered heterocyclic ring. Examples of enamines include dimethyl enamine, diethyl enamine, dipropyl enamine, dibutyl enamine, diallyl enamine, pyrrolidyne enamine, piperidyne enamine, morpholyne enamine;
oximes

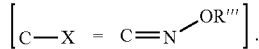

R''' can be selected from H, $C_1$-$C_6$ alkyl and benzyl. Examples of oximes include oxime, O-methyl oxime, O-benzyl oxime, O-phenylthiomethyl oxime; and
hydrazones

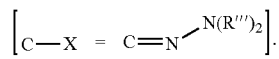

Each R''' can be independently selected from H, $C_1$-$C_6$ alkyl, $C_6$-$C_{10}$ aryl and benzyl. Examples of hydrazones include hydrazone, N,N-dimethyl hydrazone, phenylhydrazone, 2,4-dinitrophenylhydrazone, tosylhydrazone.

The term "solvate" according to this invention is to be understood as meaning any form of the compound which has another molecule (most likely a polar solvent) attached to it via non-covalent bonding. Examples of solvate include hydrates and alcoholates, e.g. methanolates.

The term "organic solvent" includes for example cyclic and acyclic ethers (e.g. $Et_2O$, $iPr_2O$, MeOtBu, 1,4-dioxane, tetrahydrofuran, methyltetrahydrofuran), hydrocarbon solvents (e.g. pentane, hexane, heptane), halogenated solvents (e.g. dichloromethane, chloroform), aromatic solvents (e.g. toluene), esters (e.g. EtOAc), nitriles (e.g. acetonitrile), amides (e.g. DMF), alcohols (e.g. methanol, ethanol, propanol), sulfoxides (DMSO) and mixtures thereof.

In a first aspect, the invention is directed to a process for the preparation of a compound of formula (I), or a solvate thereof

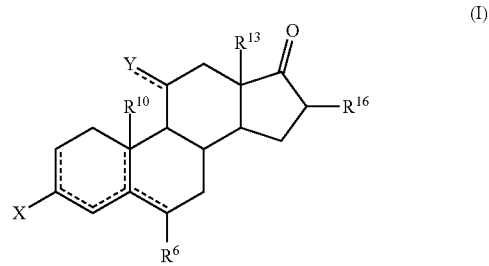

wherein X, Y, $R^6$, $R^{10}$, $R^{13}$, $R^{16}$ and $=$ are as defined above,
which comprises reacting a compound of formula (II) or a solvate thereof

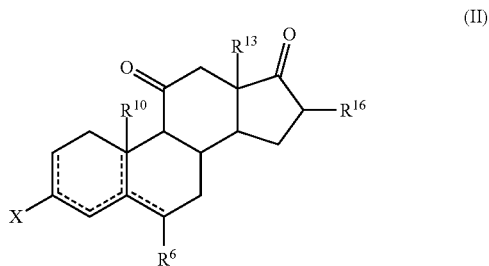

with a compound of formula (III)

wherein
Z is selected from H and $SiR'_3$, wherein each R' is independently selected from $C_1$-$C_6$ alkyl and $C_6$-$C_{10}$ aryl; and
M is selected from Li, MgBr, MgCl and MgI.

In a particular embodiment, $R^6$, $R^{10}$ and $R^{16}$ are H.

In another embodiment, $R^{13}$ is $C_1$-$C_6$ alkyl, preferably ethyl.

In another embodiment, $R^6$, $R^{10}$ and $R^{16}$ are H and $R^{13}$ is ethyl. Preferably, the compound of formula (I) or (II) is a compound of formula (Ia) or (IIa), or a solvate thereof.

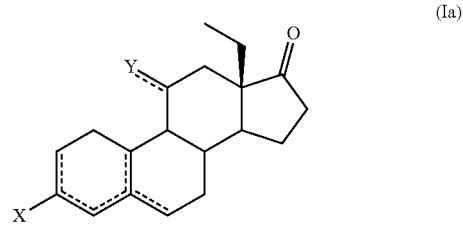

(IIa)

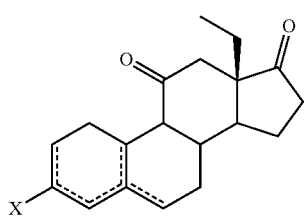

In a particular embodiment, X is H. In another embodiment, X forms together with the carbon atom to which it is bonded a ketone protecting group.

In a particular embodiment, the ketone protecting group is selected from cyclic or acyclic ketals, cyclic or acyclic dithioketals, cyclic or acyclic hemithioketals, enol ethers, enamines, oximes and hydrazones. Preferably, the ketone protecting group is selected from cyclic ketals, cyclic dithioketals, cyclic hemithioketals, enol ethers and enamines. In an embodiment, X forms together with the carbon atom to which it is bonded a group selected from:

i)

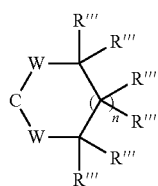

wherein each W is independently selected from O and S; n is 0, 1 or 2; and each R''' is independently selected from H and $C_1$-$C_6$ alkyl;

ii)

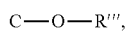

in which case there is additionally a double bond between $C_2$ and $C_3$ or between $C_3$ and $C_4$,
wherein R''' is selected from $C_1$-$C_6$ alkyl and benzyl; and iii)

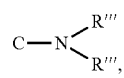

in which case there would additionally be a double bond between $C_2$ and $C_3$ or between $C_3$ and $C_4$,
wherein each R''' is independently selected from $C_1$-$C_6$ alkyl and benzyl, or the two R''' groups together with the nitrogen atom to which they are attached form a 5- or 6-membered heterocyclic ring.

In a particular embodiment, X forms together with the carbon atom to which it is bonded a group selected from:

i)

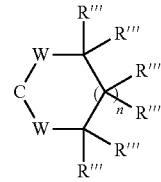

wherein each W is independently selected from O and S; n is 0; and each R''' is independently selected from H and $C_1$-$C_6$ alkyl;

ii)

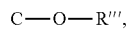

in which case there is additionally a double bond between $C_2$ and $C_3$ or between $C_3$ and Ca, wherein R''' is selected from $C_1$-$C_6$ alkyl; and iii)

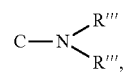

in which case there would additionally be a double bond between $C_2$ and $C_3$ or between $C_3$ and $C_4$, wherein the two R''' groups together with the nitrogen atom to which they are attached form a 5- or 6-membered heterocyclic ring.

In an embodiment, X forms together with the carbon atom to which it is bonded a group selected from 1,3-dioxolane, 1,3-dithiolane, methyl enol ether, ethyl enol ether and pyrrolidine enamine.

In a further embodiment, X forms together with the carbon atom to which it is bonded a 1,3-dioxolane group and there is a double bond between $C_5$ and $C_6$. In an embodiment, X forms together with the carbon atom to which it is bonded a 1,3-dithiolane group and there is a double bond between $C_4$ and $C_5$. In an embodiment, X forms together with the carbon atom to which it is bonded a methyl enol ether and there is a double bond between $C_2$ and $C_3$ and between $C_5$ and $C_{10}$. In an embodiment, X forms together with the carbon atom to which it is bonded an ethyl enol ether and there is a double bond between $C_3$ and $C_4$ and between $C_5$ and $C_6$. In an embodiment, X forms together with the carbon atom to which it is bonded a pyrrolidine enamine and there is a double bond between $C_3$ and $C_4$ and between $C_5$ and $C_{10}$.

In a particular embodiment, Y forms together with the carbon atom to which it is bonded a C=$CH_2$ group. In another embodiment, Y forms together with the carbon atom to which it is bonded a C(OH)$CH_2$Z group.

In an embodiment Z is H.

In another embodiment, Z is SiR'$_3$ wherein each R' is independently selected from $C_1$-$C_6$ alkyl and $C_6$-$C_{10}$ aryl (Peterson olefination reaction).

Preferably, each R' is independently selected from methyl, ethyl, n-propyl, i-propyl, n-butyl, t-butyl, n-hexyl and phenyl. In an embodiment, Z is selected from Me$_3$Si—, Et$_3$Si—, $^iPr_3Si$—, $^nPr_3Si$—, $^nHex_3Si$—, $^tBu_3Si$—, $Ph_3Si$—, $MeEt_2Si$—, $^tBuMe_2Si$—, $^tBuPh_2Si$—, $MePh_2Si$—, $EtMe_2Si$— and $PhMe_2Si$—. More preferably, Z is $Me_3Si$—.

In an embodiment of the invention, M is selected from Li and MgCl. Preferably, M is Li. In a particular embodiment, the compound of formula (III) is $Me_3Si$—$CH_2$—Li.

Reaction of the compound of formula (II) with the compound of formula (III) is preferably performed in the presence of an organic solvent, preferably, an anhydrous organic solvent, such as for example a cyclic or acyclic ether (e.g. $Et_2O$, $iPr_2O$, tBuOMe, 1,4-dioxane, tetrahydrofuran, methyltetrahydrofuran), a hydrocarbonated solvent (e.g. pentane, hexane, heptane), a halogenated solvent (e.g. dichloromethane, chloroform), an aromatic solvent (e.g. toluene) or mixtures thereof. Preferably the organic solvent is a cyclic or acyclic ether, such as $Et_2O$, $iPr_2O$, tBuOMe, 1,4-dioxane, tetrahydrofuran, methyltetrahydrofuran or mixtures thereof. In a particular embodiment, the organic solvent is tetrahydrofuran. In the present document, the term anhydrous solvent refers to a solvent containing less than 500 ppm of water.

In a particular embodiment, this reaction is performed at a temperature between −75° C. and the reflux temperature of the solvent used. In an embodiment, it is performed at a temperature of between −60° C. and 40° C., preferably between −60° C. and 25° C.

In a particular embodiment, the compound of formula (III) is present in an amount of from 1.0 to 6.0 molar equivalents with respect to the compound of formula (II), preferably from 2.0 to 4.0 molar equivalents.

The process of the invention allows selective addition of the compound of formula (III) to the keto group at position 11 of the compound of formula (II). Preferably, the reaction of the compound of formula (II) or a solvate thereof with the compound of formula (III) gives rise to the compound of formula (I) or a solvate thereof with a selectivity higher than 70%, preferably higher than 80%, preferably higher than 90%, more preferably higher than 95%, even more preferably higher than 98% (molar), with respect to the total addition products.

After reaction of the compound of formula (II), or a solvate thereof, with the compound of formula (III), a compound of formula (I) wherein Y, together with the carbon atom to which it is bonded, forms a $C(OH)CH_2Z$ group is obtained. Said compound can be isolated and used in a subsequent step of the synthesis (e.g. ethynylation, Peterson elimination, dehydration) or it can be directly treated with an acid or a base in a one-pot process to afford a compound of formula (I) wherein Y, together with the carbon atom to which it is bonded, represents $C=CH_2$. Therefore, in a particular embodiment, the process of the invention comprises:
- (a) reacting a compound of formula (II), or a solvate thereof, with a compound of formula (III) to obtain a compound of formula (I), or a solvate thereof, wherein Y together with the carbon atom to which it is bonded represents a $C(OH)CH_2Z$ group, wherein Z is selected from H and $SiR'_3$, wherein each R' is independently selected from $C_1$-$C_6$ alkyl and $C_6$-$C_{10}$ aryl; and
- (b) treating a compound of formula (I), or a solvate thereof, wherein Y together with the carbon atom to which it is bonded represents a $C(OH)CH_2Z$ group, wherein Z is selected from H and SiR's, wherein each R' is independently selected from $C_1$-$C_6$ alkyl and $C_6$-$C_{10}$ aryl, with an acid or a base to obtain a compound of formula (I), or a solvate thereof, wherein Y together with the carbon atom to which it is bonded represents $C=CH_2$.

Ethynylation Reaction (Position 17)

The compound of formula (I), or a solvate thereof, can be further ethynylated to obtain a compound of formula (IV), or a solvate thereof,

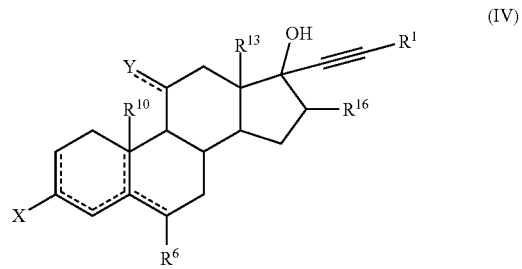

wherein
- Y, $R^6$, $R^{10}$, $R^{13}$, $R^{16}$ and ⸺ are as defined above;
- X represents H or it forms together with the carbon atom to which it is bonded a ketone group or a ketone protecting group; and
- $R^1$ is selected from H and $SiR''_3$, wherein each R'' is independently selected from $C_1$-$C_6$ alkyl, $C_6$-$C_{10}$ aryl and halogen.

The ethynylation reaction can be performed either before or after generating the $C=CH_2$ group at position 11 of the steroid. Hence, in a particular embodiment, the process of the invention comprises:
- (a) reacting a compound of formula (II), or a solvate thereof, with a compound of formula (III) to obtain a compound of formula (I), or a solvate thereof, wherein Y together with the carbon atom to which it is bonded represents a $C(OH)CH_2Z$ group;
- (b) treating a compound of formula (I), or a solvate thereof, wherein Y together with the carbon atom to which it is bonded represents a $C(OH)CH_2Z$ group, with an acid or a base to obtain a compound of formula (I), or a solvate thereof, wherein Y together with the carbon atom to which it is bonded represents $C=CH_2$; and
- (c) ethynylating a compound of formula (I), or a solvate thereof, wherein Y together with the carbon atom to which it is bonded represents $C=CH_2$, to obtain a compound of formula (IV), or a solvate thereof, wherein Y together with the carbon atom to which it is bonded represents $C=CH_2$.

In another embodiment, the process of the invention comprises:
- (a) reacting a compound of formula (II), or a solvate thereof, with a compound of formula (III) to obtain a compound of formula (I), or a solvate thereof, wherein Y together with the carbon atom to which it is bonded represents a $C(OH)CH_2Z$ group;
- (b) ethynylating a compound of formula (I), or a solvate thereof, wherein Y together with the carbon atom to which it is bonded represents a $C(OH)CH_2Z$ group, to obtain a compound of formula (IV), or a solvate thereof, wherein Y together with the carbon atom to which it is bonded represents a $C(OH)CH_2Z$ group; and
- (c) treating a compound of formula (IV), or a solvate thereof, wherein Y together with the carbon atom to which it is bonded represents a $C(OH)CH_2Z$ group, with an acid or a base to obtain a compound of formula (IV), or a solvate thereof, wherein Y together with the carbon atom to which it is bonded represents C=CH₂.

The ethynylation reaction can be performed under reaction conditions disclosed in the prior art for the alkynylation of steroids. In a particular embodiment, the ethynylation reaction is carried out by treating the compound of formula (I), or a solvate thereof, with a compound of formula (V)

(V)

wherein

M' is selected from Li, Na, K, MgBr, MgCl and MgI; and

R¹ is selected from H and SiR"₃, wherein each R" is independently selected from $C_1$-$C_6$ alkyl, $C_6$-$C_{10}$ aryl and halogen.

In a particular embodiment, each R" is independently selected from $C_1$-$C_6$ alkyl, phenyl and Cl. In a further embodiment, each R" is independently selected from methyl, ethyl, n-propyl, i-propyl, n-butyl, t-butyl, n-hexyl, Ph and Cl. Preferably, —SiR"₃ is selected from Et₃Si—, Me₃Si—, $^i$Pr₃Si—, $^n$Pr₃Si—, $^n$Hex₃Si—, $^t$Bu₃Si—, Ph₃Si—, C₁₃Si—, MeEt₂Si—, $^t$BuMe₂Si—, $^t$BuPh₂Si—, Cl$^i$Pr₂Si—, ClMe₂Si—, MePh₂Si—, EtMe₂Si—, EtCl₂Si—, MeCl₂Si—, PhMe₂Si— and PhMeClSi—. More preferably, —SiR"₃ is selected from Me₃Si—, Et₃Si—, Pr₃Si—, PhMe₂Si—, $^t$BuMe₂Si— and $^t$BuPh₂Si—. Still more preferably, —SiR"₃ is Me₃Si—.

In an embodiment, R¹ is H.

In a preferred embodiment, R¹ is a SiR"₃ group. Preferably, R¹ is a SiR"₃ group wherein each R" is independently selected from $C_1$-$C_6$ alkyl, such as SiMe₃.

In an embodiment, M' is Li. Preferably, M' is Li and R¹ is a SiR"₃ group.

In another embodiment, M' is selected from MgBr, MgCl and MgI. Preferably, M' is selected from MgBr, MgCl and MgI and R¹ is H.

The ethynylation reaction is preferably performed in the presence of an organic solvent, preferably, an anhydrous organic solvent, such as for example a cyclic or acyclic ether (e.g. Et₂O, iPr₂O, 1,4-dioxane, tetrahydrofuran, methyltetrahydrofuran), a hydrocarbon solvent (e.g. pentane, hexane, heptane), a halogenated solvent (e.g. dichloromethane, chloroform), an aromatic solvent (e.g. toluene) or mixtures thereof. Preferably the organic solvent is a cyclic or acyclic ether, such as Et₂O, iPr₂O, 1,4-dioxane, tetrahydrofuran, methyltetrahydrofuran; a hydrocarbon solvent, such as pentane, hexane, heptane; or mixtures thereof.

In a particular embodiment, this reaction is performed at a temperature between −75° C. and the reflux temperature of the solvent used. In an embodiment, it is performed at a temperature of between −60° C. and 50° C., preferably between −30° C. and 30° C.

In a particular embodiment, the compound of formula (V) is present in an amount of from 1.0 to 5.0 molar equivalents with respect to the compound of formula (I), preferably from 1.1 to 3.0 molar equivalents.

When X in the compound of formula (I), or a solvate thereof, forms together with the carbon atom to which it is bonded a ketone protecting group, depending on the ethynylation reaction conditions, the ketone protecting group and/or the acid or based used to generate the C=CH₂ group at position 11, then a compound of formula (IV), or a solvate thereof, wherein X forms, together with the carbon atom to which it is bonded, a ketone protecting group or a ketone group can be obtained.

In an embodiment of the invention, a compound of formula (IV), or a solvate thereof, wherein X forms, together with the carbon atom to which it is bonded, a ketone protecting group is maintained after the ethynylation reaction.

In a particular embodiment, a compound of formula (IV), or a solvate thereof, wherein X forms, together with the carbon atom to which it is bonded, a ketone group is obtained after treating the compound of formula (IV), or a solvate thereof, with an acid or a base to generate the C=CH₂ group.

When R¹ is a SiR"₃ group, desilylation can be performed to obtain a compound of formula (IV), or a solvate thereof, wherein R¹ is H.

This desilylation reaction can be carried out by methods known in the prior art (e.g. T. H. Greene and P. G. M Wuts, Protective Groups in Organic Synthesis, 4$^{th}$ edition, John Wiley & Sons, 2007). In a particular embodiment, the desilylation is carried out using fluorine salts or bases in the presence of water, an organic solvent or mixtures thereof. Fluorine salts such as pyridinium fluoride, potassium fluoride or ammonium fluoride; or inorganic bases, such as sodium hydroxide, lithium hydroxide, potassium hydroxide or potassium carbonate can be used. In a particular embodiment, the desilylation reaction is carried out in the presence of an inorganic base and an organic solvent.

In a particular embodiment, the desilylation reaction is performed at a temperature between −60 and +100° C. In another embodiment, it is performed at a temperature between −10 and +60° C., preferably between 1° and 35° C.

Desilylation reaction can be performed either before or after the generation of the C=CH₂ group at position 11 and either before or after cleavage of the ketone protecting group.

Generation of the C=CH₂ Group (Position 11)

In an embodiment, a compound of formula (I), or a compound of formula (IV), or a solvate thereof, wherein Y together with the carbon atom to which it is bonded represents a C(OH)CH₂Z group, is treated with an acid or a base to obtain a compound of formula (I), or a compound of formula (IV), or a solvate thereof, wherein Y together with the carbon atom to which it is bonded represents C=CH₂.

When Z is a SiR'₃ group, treatment with an acid or a base gives rise to a compound wherein Y together with the carbon atom to which it is bonded represents C=CH₂ (Peterson elimination reaction).

When Z is H, treatment with an acid gives rise to a compound wherein Y together with the carbon atom to which it is bonded represents C=CH₂ (dehydration reaction).

Suitable acids include organic acids, inorganic acids, Lewis acids and mixtures thereof. Examples of suitable acids include acetic acid, trifluoroacetic acid, chloroacetic acid, methanesulfonic acid, trifluoromethanesulfonic acid, formic acid, propionic acid, butyric acid, malic acid, citric acid, benzoic acid, p-toluenesulfonic acid, oxalic acid, succinic acid, hydrochloric acid, hydrobromic acid, hydrofluoric acid, perchloric acid, chloric acid, sulfuric acid, nitric acid, phosphoric acid, ZnCl₂, AlCl₃ and BF₃. In a particular embodiment, the acid is selected from acetic acid, trifluoroacetic acid, methanesulfonic acid, trifluoromethanesulfonic acid, hydrochloric acid, hydrobromic acid, perchloric acid, sulfuric acid and mixtures thereof.

Suitable bases include e.g. alkali metal hydrides, alkali metal alkoxides, alkali metal hydroxides, such as sodium hydride, potassium hydride, sodium methoxide, sodium ethoxide, sodium t-butoxide, potassium methoxide, potassium ethoxide, potassium t-butoxide, sodium hydroxide and potassium hydroxide.

In a particular embodiment, a compound of formula (I), or a solvate thereof, wherein Y together with the carbon atom to which it is bonded represents a $C(OH)CH_2Z$ group, is treated with an acid or a base before the ethynylation reaction to afford a compound of formula (I), or a solvate thereof, wherein Y together with the carbon atom to which it is bonded represents $C=CH_2$.

In another embodiment, treatment with an acid or a base is performed after the ethynylation reaction so that a compound of formula (IV), or a solvate thereof, wherein Y together with the carbon atom to which it is bonded represents a $C(OH)CH_2Z$ group, is converted into a compound of formula (IV), or a solvate thereof, wherein Y together with the carbon atom to which it is bonded represents $C=CH_2$. In this case, depending on the acid or base employed, the reaction conditions and/or the ketone protecting group, a compound of formula (IV), or a solvate thereof, wherein X forms, together with the carbon atom to which it is bonded, a ketone protecting group or a ketone group can be obtained.

In a preferred embodiment, the acid or based used to generate the $C=CH_2$ group at position 11 also allow cleavage of the ketone protecting group at position 3 so that it is obtained a compound of formula (IV) wherein Y, together with the carbon atom to which it is bonded, represents $C=CH_2$ and X, together with the carbon atom to which it is bonded, represents a ketone group.

Cleavage of the Ketone Protecting Group (Position 3)

In order to obtain a compound of formula (IV) wherein X is hydrogen or forms, together with the carbon atom to which it is bonded, a ketone group, a deprotection step of the ketone protecting group may be needed. Cleavage of the ketone protecting group can be carried out by any conventional means known in the art (e.g. T. H. Greene and P. G. M Wuts, Protective Groups in Organic Synthesis, $4^{th}$ edition, John Wiley & Sons, 2007).

For example, when the ketone protecting group is a ketal, a thioketal or an enol ether, it can be cleaved to regenerate de 3-keto group in acid media.

When the ketone protecting group is an enamine, it can be cleaved by hydrolysis in acid or basic media according to well established procedures of the state of the art.

When the ketone protecting group is a dithioketal, it can be cleaved by oxidation or in the presence of a Lewis acid. In addition, when the ketone protecting group is a dithioketal it can be removed under reducing conditions to obtain a compound wherein X is H.

In a particular embodiment, the ketone protecting group is cleaved under the reactions conditions employed to generate the $CH=CH_2$ group at position 11, so that both processes occur in a single step.

In view of the information provided herein, the skilled person will appreciate that different sequences of steps can be used and that further synthetic steps might be needed to put the invention into practice.

For example, to obtain a compound of formula (IV) wherein $R^1$ is H and X is hydrogen or forms, together with the carbon atom to which it is bonded, a ketone group, it might be necessary to carry out one or both of the following steps:
(i) cleavage of the ketone protecting group to afford a compound of formula (IV), or a solvate thereof, wherein X is H or forms together with the carbon atom to which it is bonded a ketone group,
(ii) removal of the $SiR''_3$ group to afford a compound of formula (IV), or a solvate thereof, wherein $R^1$ is H.

These steps can be carried out in any order. That is, if both steps are carried out, step (i) can be carried out either before or after step (ii).

In order to convert a compound of formula (I), or a solvate thereof, wherein Y together with the carbon atom to which it is bonded represents a $C(OH)CH_2Z$, into a compound of formula (IV), or a solvate thereof, wherein $R^1$ is H, X forms together with the carbon atom to which it is bonded a ketone group and Y together with the carbon atom to which it is bonded represents $CH=CH_2$, any of the following sequences of steps can be followed:
ethynylation/generation of the $CH=CH_2$ group/if needed, desilylation of the alkyne/if needed, cleavage of the ketone protecting group; or
ethynylation/generation of the $CH=CH_2$ group/if needed, cleavage of the ketone protecting group/if needed, desilylation of the alkyne; or
ethynylation/if needed, desilylation of the alkyne/generation of the $CH=CH_2$ group/if needed, cleavage of the ketone protecting group; or
ethynylation/generation of the $CH=CH_2$ group/if needed, desilylation of the alkyne/if needed, cleavage of the ketone protecting group; or
generation of the $CH=CH_2$ group/ethynylation/if needed, desilylation of the alkyne/if needed, cleavage of the ketone protecting group; or
generation of the $CH=CH_2$ group/ethynylation/if needed, cleavage of the ketone protecting group/if needed, desilylation of the alkyne; or
ethynylation/if needed, cleavage of the ketone protecting group/generation of the $CH=CH_2$ group/if needed, desilylation of the alkyne; or
ethynylation/if needed, cleavage of the ketone protecting group/if needed, desilylation of the alkyne/generation of the $CH=CH_2$ group.

In order to convert a compound of formula (I), or a solvate thereof, wherein Y together with the carbon atom to which it is bonded represents a $C(OH)CH_2Z$, into a compound of formula (IV), or a solvate thereof, wherein $R^1$ is H, X is hydrogen and Y together with the carbon atom to which it is bonded represents $CH=CH_2$, any of the following sequences of steps can be followed:
ethynylation/generation of the $CH=CH_2$ group/if needed, desilylation of the alkyne/if needed, reductive elimination of the ketone protecting group; or
ethynylation/generation of the $CH=CH_2$ group/if needed, reductive elimination of the ketone protecting group/if needed, desilylation of the alkyne; or
ethynylation/if needed, desilylation of the alkyne/generation of the $CH=CH_2$ group/if needed, reductive elimination of the ketone protecting group; or
ethynylation/generation of the $CH=CH_2$ group/if needed, desilylation of the alkyne/if needed, reductive elimination of the ketone protecting group; or
generation of the $CH=CH_2$ group/ethynylation/if needed, desilylation of the alkyne/if needed, reductive elimination of the ketone protecting group; or
generation of the $CH=CH_2$ group/ethynylation/if needed, reductive elimination of the ketone protecting group/if needed, desilylation of the alkyne; or
ethynylation/if needed, reductive elimination of the ketone protecting group/generation of the $CH=CH_2$ group/if needed, desilylation of the alkyne; or ethynylation/if needed, reductive elimination of the ketone protecting group/if needed, desilylation of the alkyne/generation of the CH=CH$_2$ group.

Synthesis of Etonogestrel and Desogestrel

Compounds of formula (I) obtained by the process of the invention are useful intermediates in the preparation of several pharmaceutically active agents, such as e.g. Etonogestrel and Desogestrel.

In a further aspect, the invention is directed to a process for the preparation of Etonogestrel, or Desogestrel, or a solvate thereof, which comprises reacting a compound of formula (II), or a solvate thereof, as defined herein with a compound of formula (III) as defined herein.

In a particular embodiment, Etonogestrel can be obtained by a process which comprises:
  (a) reacting a compound of formula (IIa), or a solvate thereof,

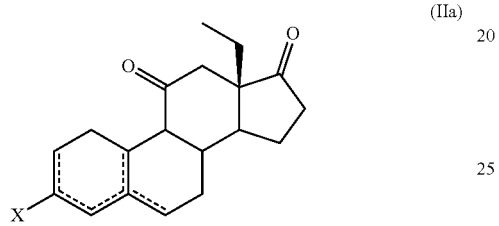

(IIa)

wherein X forms together with the carbon atom to which it is bonded a ketone protecting group;
with a compound of formula (III)

(III)

wherein ≡, M and Z are as defined herein;
to afford a compound of formula (Ia-1) or a solvate thereof

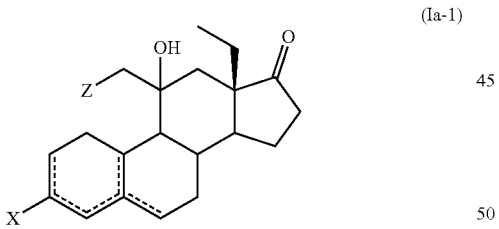

(Ia-1)

(b) treating a compound of formula (Ia-1), or a solvate thereof, with an acid or a base to afford a compound of formula (Ia-2), or a solvate thereof,

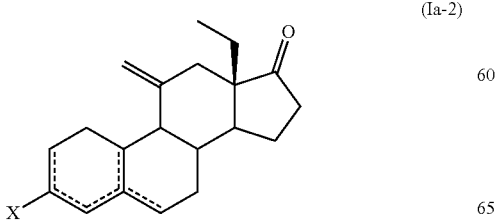

(Ia-2)

(c) ethynylating a compound of formula (Ia-2), or a solvate thereof, to afford a compound of formula (IVa-1), or a solvate thereof

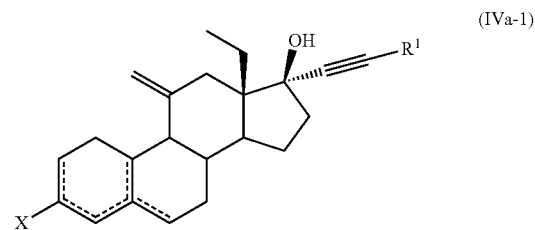

(IVa-1)

wherein
  X forms together with the carbon atom to which it is bonded a ketone group or a ketone protecting group
  $R^1$ is selected from H and SiR"$_3$, wherein each R" is independently selected from $C_1$-$C_6$ alkyl, $C_6$-$C_{10}$ aryl and halogen; and
(d) if necessary, carrying out one or both of the following steps in any order:
  (i) if X forms together with the carbon atom to which it is bonded a ketone protecting group, cleavage of the ketone protecting group to afford a compound of formula (IVa-1), or a solvate thereof, wherein X forms together with the carbon atom to which it is bonded a ketone group,
  (ii) if $R^1$ is a SiR"$_3$ group, removal of the SiR"$_3$ group to afford a compound of formula (IVa-1), or a solvate thereof, wherein $R^1$ is H.

In another embodiment, Etonogestrel can be obtained by a process which comprises:
  (a) reacting a compound of formula (IIa), or a solvate thereof,

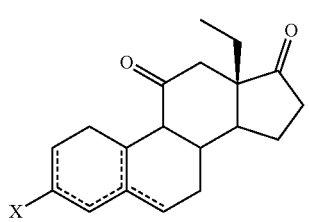

(IIa)

wherein X forms together with the carbon atom to which it is bonded a ketone protecting group;
with a compound of formula (III)

(III)

wherein ≡, M and Z are as defined herein;
to afford a compound of formula (Ia-1), or a solvate thereof,

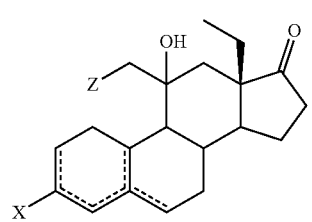

(Ia-1)

(b) ethynylating a compound of formula (Ia-1), or a solvate thereof, to afford a compound of formula (IVa-2), or a solvate thereof

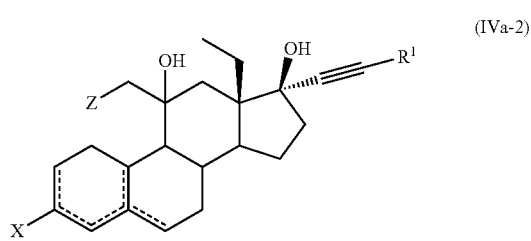

(IVa-2)

wherein $R^1$ is selected from H and $SiR''_3$, wherein each $R''$ is independently selected from $C_1$-$C_6$ alkyl, $C_6$-$C_{10}$ aryl and halogen;

(c) treating a compound of formula (IVa-2), or a solvate thereof, with an acid or a base to afford a compound of formula (IVa-1), or a solvate thereof

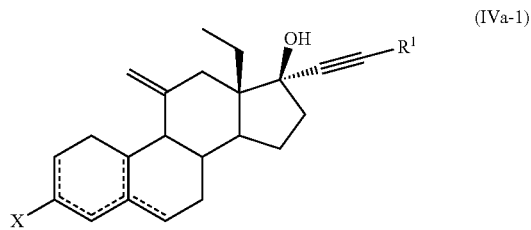

(IVa-1)

wherein
X forms together with the carbon atom to which it is bonded a ketone group or a ketone protecting group
$R^1$ is selected from H and $SiR''_3$, wherein each $R''$ is independently selected from $C_1$-$C_6$ alkyl, $C_6$-$C_{10}$ aryl and halogen; and (d) if necessary, carrying out one or both of the following steps in any order:
  (i) if X forms together with the carbon atom to which it is bonded a ketone protecting group, cleavage of the ketone protecting group to afford a compound of formula (IVa-1), or a solvate thereof, wherein X forms together with the carbon atom to which it is bonded a ketone group,
  (ii) if $R^1$ is a $SiR''_3$ group, removal of the $SiR''_3$ group to afford a compound of formula (IVa-1), or a solvate thereof, wherein $R^1$ is H.

In another embodiment, Desogestrel can be obtained by a process which comprises:
(a) obtaining a compound of formula (IVa-1), or a solvate thereof, by any of the processes defined above wherein X forms together with the carbon atom to which it is bonded a cyclic dithioketal group;
(b) cleavage of the cyclic dithioketal group under reducing conditions to obtain a compound of formula (IVb-1), or a solvate thereof; and
(c) if $R^1$ is a $SiR''_3$ group, removal of the $SiR''_3$ group to afford a compound of formula (IVb-1), or a solvate thereof, wherein $R^1$ is H, either before or after step (b).

In a further embodiment of the invention, Desogestrel can be obtained by a process comprising:
(a) reacting compound (12), or a solvate thereof,

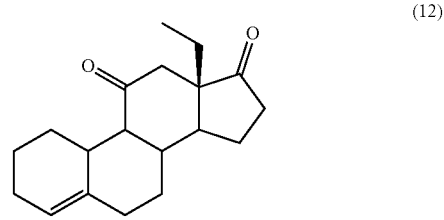 [SMILES: CC[C@]12CC(=O)C3C4CCCC=C4CCC3C1CCC2=O]

(12)

with a compound of formula (III)

(III)

wherein M and Z are as defined herein;
to afford a compound of formula (Ib-1) or a solvate thereof

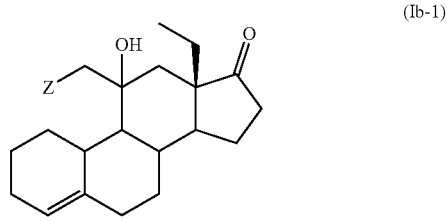

(Ib-1)

(b) treating a compound of formula (Ib-1), or a solvate thereof, with an acid or a base to afford a compound of formula (Ib-2), or a solvate thereof,

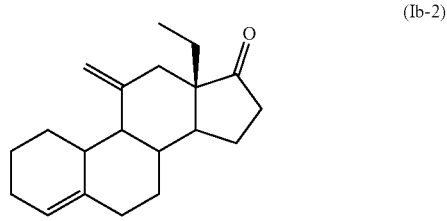 [SMILES: C=C1C[C@]2(CC)C(=O)CCC2C2CCC3=CCCCC3C12]

(Ib-2)

(c) ethynylating a compound of formula (Ib-2), or a solvate thereof, to afford a compound of formula (IVb-1), or a solvate thereof

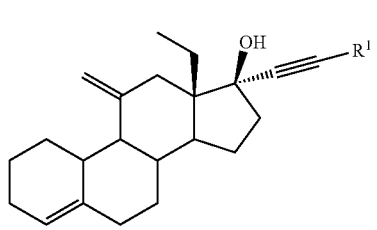

(IVb-1)

wherein R¹ is selected from H and SiR"₃, wherein each R" is independently selected from $C_1$-$C_6$ alkyl, $C_6$-$C_{10}$ aryl and halogen; and (d) if R¹ is a SiR"₃ group, removing SiR"₃ group to afford Desogestrel, or a solvate thereof.

Compounds of Formula (Ic) and (IVc)

In another aspect, the invention is directed to a compound of formula (Ic), or a solvate thereof,

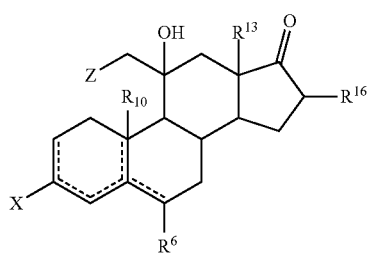

(Ic)

wherein X, Z, R⁶, R¹⁰, R¹³, R¹⁶ and ⁼ are as defined herein.

Preferred embodiments for X, Z, R⁶, R¹⁰, R¹³, R¹⁶ and ⁼ are as defined above.

In a particularly preferred embodiment, in the compound of formula (Ic) Z is SiR'₃ wherein each R' is independently selected from $C_1$-$C_6$ alkyl and $C_6$-$C_{10}$ aryl. Preferred embodiments for R' are as defined above.

In another particular embodiment, the compound of formula (Ic) does not represent:

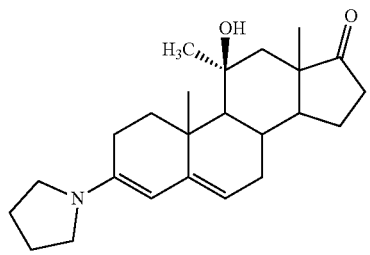 [SMILES: CC12C[C@](C)(O)C3C(CC=C4C=C(N5CCCC5)CCC43C)C1CCC2=O]

(11α-methyl-3-(N-pyrrolidyl)-Δ³,⁵-androstadien-11β-ol-17-one),

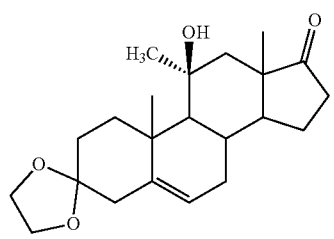 [SMILES: CC12C[C@](C)(O)C3C(CC=C4CC5(CCC43C)OCCO5)C1CCC2=O]

(11α-methyl-Δ⁵-androsten-11β-ol-3,17-dione-3-monoethylene ketal), or

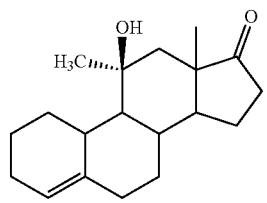 [SMILES: CC12C[C@](C)(O)C3C4CCCC=C4CCC3C1CCC2=O]

(11α-methyl-11β-hydroxy-Δ⁴-estren-17-one).

In a particular embodiment, the compound of formula (Ic) is a compound of formula (Ia-1), or a compound of formula (Ib-1), or a solvate thereof.

In a preferred embodiment, the compound of formula (Ic) is selected from:

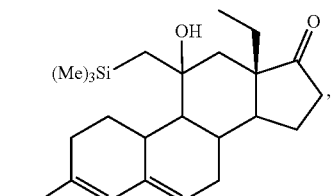

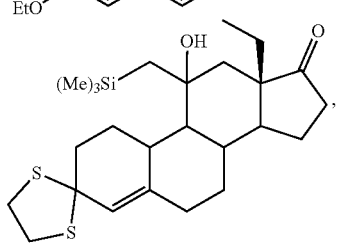

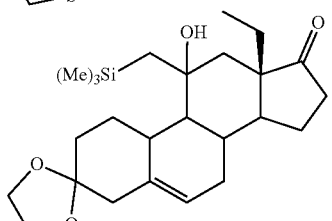

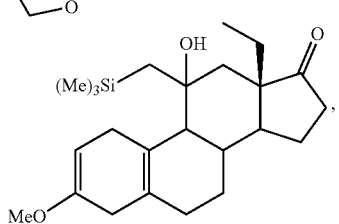

-continued

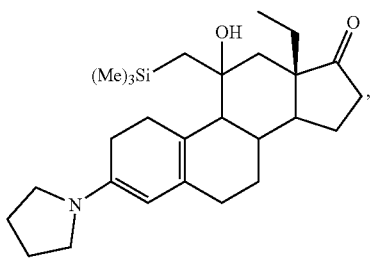

and

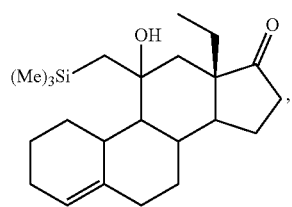

or a solvate thereof.

In another aspect, the invention is directed to a compound of formula (IVc), or a solvate thereof,

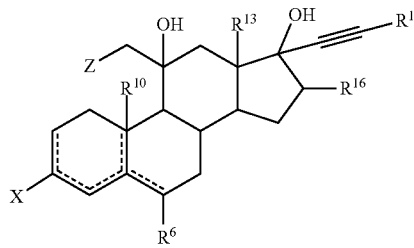

(IVc)

wherein X, Z, $R^1$, $R^6$, $R^{10}$, $R^{13}$, $R^{16}$ and ≡ are as defined herein.

Preferred embodiments for X, Z, $R^1$, $R^6$, $R^{10}$, $R^{13}$, $R^{16}$ and ≡ are as defined above.

In a particularly preferred embodiment, in the compound of formula (IVc) $R^1$ is $SiR''_3$, wherein each R'' is independently selected from $C_1$-$C_6$ alkyl, $C_6$-$C_{10}$ aryl and halogen. Preferred embodiments for R'' are as defined above.

In a particular embodiment, the compound of formula (IVc) does not represent:

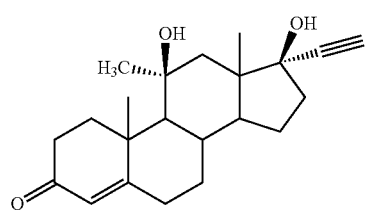 [SMILES: C#C[C@]1(O)CCC2C3CCC4=CC(=O)CCC4(C)C3[C@@](C)(O)CC21C]

(4-androsten-11α-methyl-11β,17β-diol-17α-ethynyl-3-one),

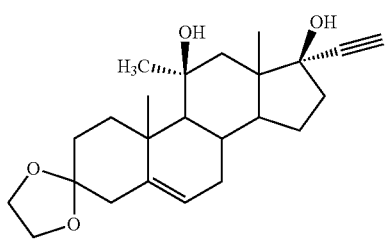 [SMILES: C#C[C@]1(O)CCC2C3CC=C4CC5(CCC4(C)C3[C@@](C)(O)CC21C)OCCO5]

(5-androsten-11α-methyl-11,17β-diol-17α-ethynyl-3-one ethyleneketal),

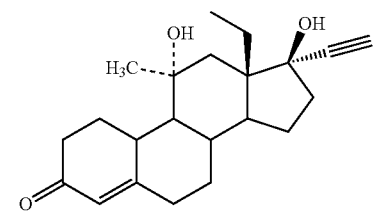 [SMILES: C#C[C@]1(O)CCC2C3CCC4=CC(=O)CCC4C3[C@](C)(O)C[C@@]21CC]

(18,19-dinorpregn-5-en-20-yn-3-one, 13-ethyl-11,17ρ-dihydroxy-11-methyl, cyclic 1,2-ethanediyl acetal), or

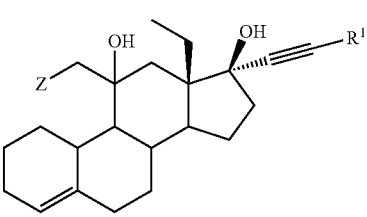

(18,19-dinorpregn-4-en-20-yn-3-one, 13-ethyl-11,17β-dihydroxy-11-methyl).

In a particular embodiment, the compound of formula (IVc) is a compound of formula (IVa-2), or a compound of formula (IVb-2), or a solvate thereof.

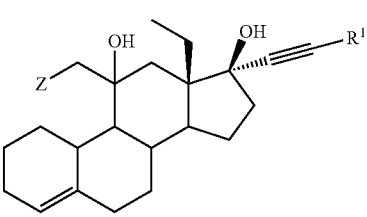

(IVb-2)

In a preferred embodiment, the compound of formula (IVc) is selected from:

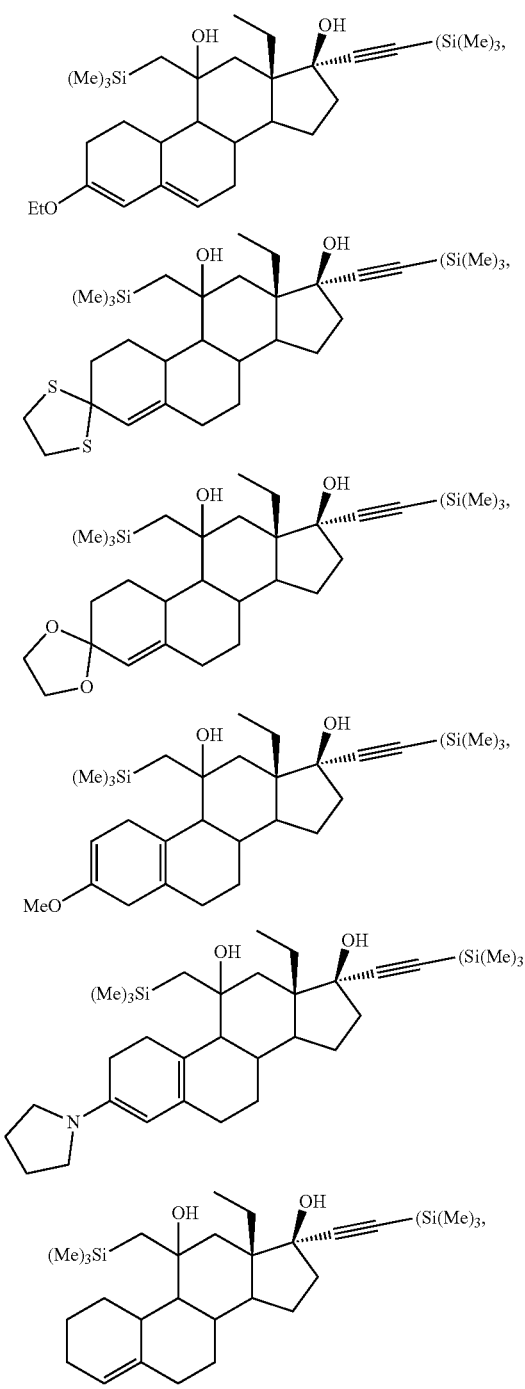
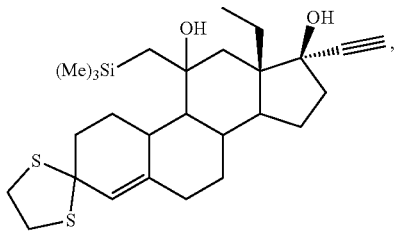
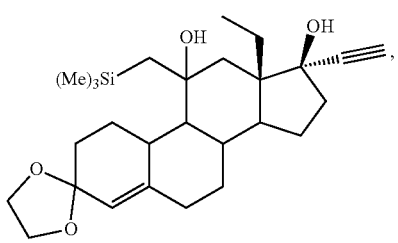
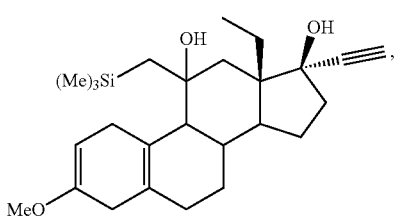
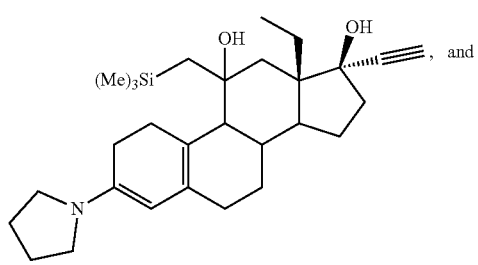
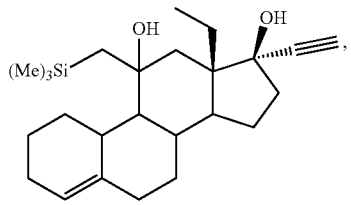
or a solvate thereof.
It should be understood that the scope of the present disclosure includes all the possible combinations of embodiments disclosed herein.
The following examples illustrate the invention and should not be considered as limitative of the invention.

EXAMPLES

Example 1. Synthesis of 18-methyl-estra-4-en-3,11,17-trione (2-Swern oxidation)

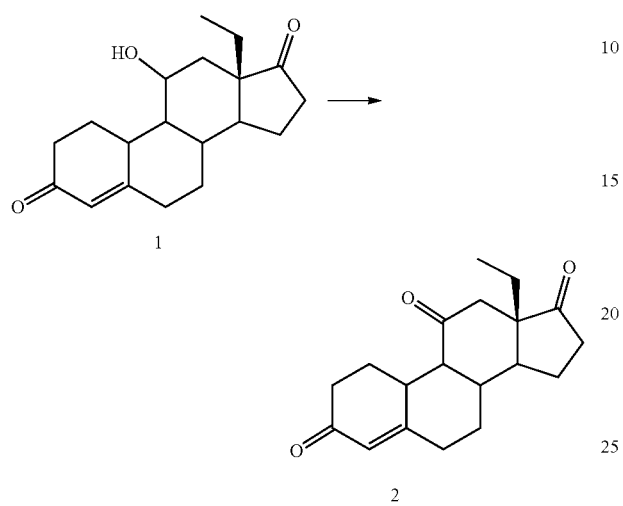

Oxalyl chloride was added to 540 mL of DCM at −20° C. The solution was cooled down at −45° C. and then DMSO (63 mL) diluted in 450 mL of DCM was dropwise added keeping the temperature below −35° C. After addition was complete, the reaction mixture was stirred 20 min at −40° C. Then, 45 g of compound 1 dissolved in 450 mL of DCM were then added keeping the temperature below −35° C. The reaction mixture was kept at −40° C. for 30 min, then DIPEA (235 mL) was quickly added and the cold bath removed allowing to warm up to room temperature (1.5 h). 675 mL of 3.3% solution of acetic acid were added and the aqueous phase was separated. The organic phase was washed with 315 mL of a solution of NaHCO₃ 7%, separated and concentrated under vacuum to a volume of 150 mL. 150 mL of IPA were added and reduced the volume to 150 mL. The operation was repeated two more times to reach a final volume of 150 mL. The resulting suspension was stirred in an ice bath for 30 min and then filtered, the solid was washed with 45 mL of cold IPA and dried under vacuum at 40° C. 39.8 g of compound 2 were obtained as white solid (yield=89.5%).

Example 2. Synthesis of 18-methyl-estra-4-en-3,11,17-trione (2-Parikh-Doering Oxidation)

15 g of compound 1 were dissolved in 40 mL of DMSO and then 71 mL of TEA were added. The solution was heated at 30° C., and a solution of SO₃Py (79 g) in 70 mL of DMSO were added. The reaction mixture was stirred at 30° C. for 3 h, and then poured over a solution of 117 mL of glacial acetic acid in 234 mL of water forming a precipitate. The suspension was cooled in an ice bath for 1 h, and filtered. The solid was suspended in 80 mL of IPA and heated to complete dissolution and then cooled down at 0° C. The resulting solid was filtered and dried under vacuum at 40° C. to yield 13 g of compound 2 (81%).

Example 3. Synthesis of Compound 3 (Ketone Protection)

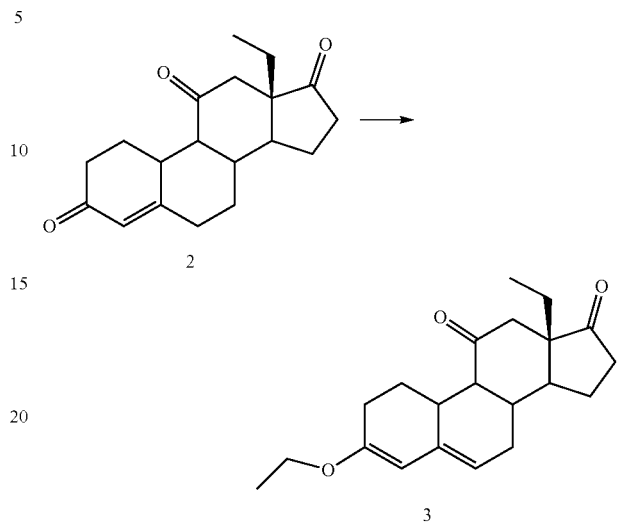

18 g of compound 2 were dissolved in 140 mL of THF, then 30 mL of TEOF and 900 mg of pTsOH were added. The reaction mixture was stirred at 25° C. for 3 h. Then 2 mL of TEA were added, and 90 mL of solution of NaHCO₃ 7%. The aqueous phase was extracted with 50 mL EtOAc. The combined organic phases were concentrated until a wet solid was obtained, 90 mL of ethanol were added and concentrated to a volume of 40 mL, cooled in an ice bath and filtered. The solid was washed with 90 mL of cold ethanol and dried under vacuum at 40° C., to yield 14.7 g of compound 3 (75%).

Example 4. Synthesis of Compound 4 (Peterson Olefination)

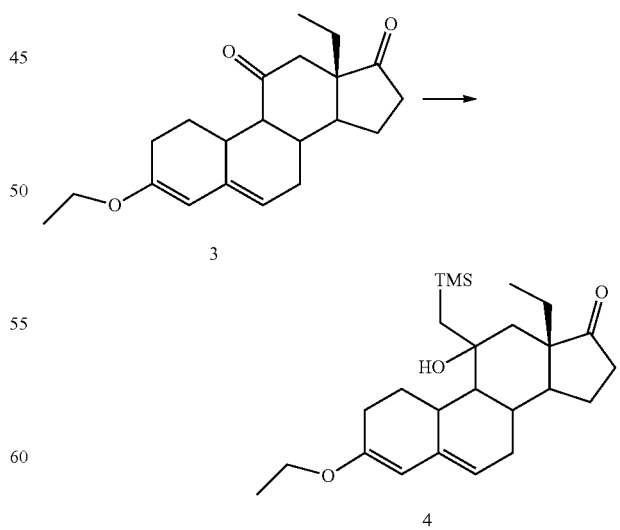

10 g of compound 3 were dissolved in 50 mL of THF and cooled down at −40° C. Then 88 mL of trimethylsilyl methyl lithium were slowly added, keeping the temperature below −35° C., and the mixture stirred for 1 h further after addition was complete. Then 200 mL of solution of NaHCO$_3$ 7% were added, separated and the aqueous phase was extracted with 100 mL EtOAc. The combined organic phases were concentrated to 30 mL, 30 mL of ethanol were added and the solvent was evaporated to a final volume of 30 mL. The operation was repeated two more times, then the suspension was cooled in an ice bath for 1 h. The solid was filtered, washed with 10 mL of cold ethanol and dried under vacuum at 40° C., to yield 10.4 g of compound 4 (83% yield).

$^1$H NMR (400 MHz, CDCl$_3$): δ 0.09 (s, 9H); 0.82 (t, 3H); 1.17-1.39 (m, 10H); 1.63-1.66 (m, 1H); 1.68-1.72 (m, 1H); 1.84-1.87 (m, 2H); 1.92-2.12 (m, 3H); 2.21-2.35 (d, 3H); 2.39-2.51 (m, 4H); 3.69-3.79 (m, 2H); 5.19 (s, 1H) 5.31 (d, 1H).

$^{13}$C NMR (100 MHz, CDCl$_3$): δ 1.1; 8.4; 14.7; 18.5; 21.3; 29.2; 30.7; 31.2; 35.1; 35.6; 37.1; 38.4; 43.4; 50.7; 51.5; 53.3; 62.4; 100.1; 117.3; 137.8; 156.2; 218.8.

Example 5. Synthesis of Compound 5 (Ethynylation Reaction)

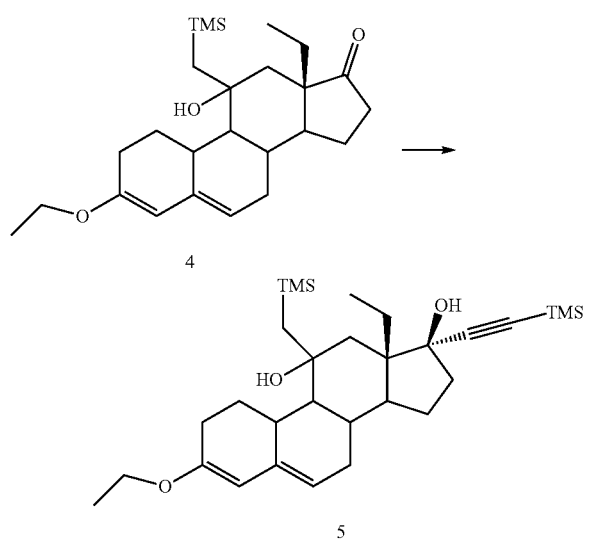

To a solution of hexyllithium (76 mL) in heptane (100 mL) cooled at 0° C., a solution of trimethylsilyl acetylene (30 mL) in 100 ml of a mixture of THF/heptanes 1/3 was slowly added. The reaction mixture was stirred at 0° C. for 30 min, then a solution of compound 4 (10 g) in 100 mL of THF was added and the mixture stirred for 1 h further. Water (200 mL) was added to quench the excess of lithium reagent and the organic phase concentrated under vacuum. The residue (containing 85% of compound 5 and 15% of compound 4, maximum level of conversion obtained) was purified on silica gel with EtOAc/heptanes 1/9, affording pure compound 5 as an oil.

$^1$H NMR (400 MHz, CDCl$_3$): δ 0.07 (s, 9H); 0.12 (s, 9H) 0.83-0.85 (m, 1H); 1.12-1.18 (m, 5H); 1.22-1.28 (m, 6H); 1.33-1.38 (m, 3H); 1.58-1.66 (m, 4H); 1.91 (d, 1H); 1.98-2.09 (m, 3H); 2.17 (d, 1H); 2.27-2.36 (m, 4H); 3.68-3.77 (m, 2H); 5.18 (s, 1H) 5.29 (d, 1H).

$^{13}$C (100 MHz, CDCl$_3$): δ 1.1; 8.4; 14.7; 18.5; 21.3; 29.2; 30.7; 31.2; 35.1; 35.6; 37.1; 38.4; 43.4; 50.7; 51.5; 53.3; 62.4; 100.1; 117.3; 137.8; 156.2; 218.8.

Example 6. Synthesis of Etonogestrel (Ethynylation Reaction)

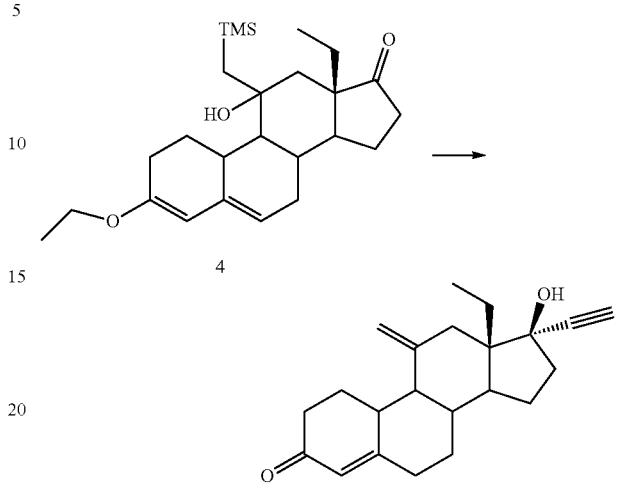

1.9 g of compound 4 were dissolved in 19 mL of THF, cooled down at 0° C. and 30 mL of LaCl$_3$*2LiCl were added, followed by slow addition of ethynylmagnesium chloride (120 mL) keeping the temperature below 10° C. After 15 h, 2.5 mL of TEA and 250 mL of solution of NaHCO$_3$ 7% were added. The aqueous phase was extracted with EtOAc 50 mL X 2, and the combined organic phases were washed with brine. The solvent was evaporated under reduced pressure to a volume of 20 mL and 40 mL of methanol were added. It was concentrated to 20 mL and repeated twice. The final methanol solution was treated with 2 mL of HCl, stirred at 25° C. for 1 h, and 2 mL of solution of NaHCO$_3$ 7% were added. Addition of 1 mL of water promoted the precipitation of a solid. It was filtered, washed with 4 mL of water and dried under vacuum at 40° C., yielding 2 g of crude Etonogestrel as brown solid (hplc purity 94%).

Example 7. Synthesis of Etonogestrel (One-Pot Ethynylation/Deprotection)

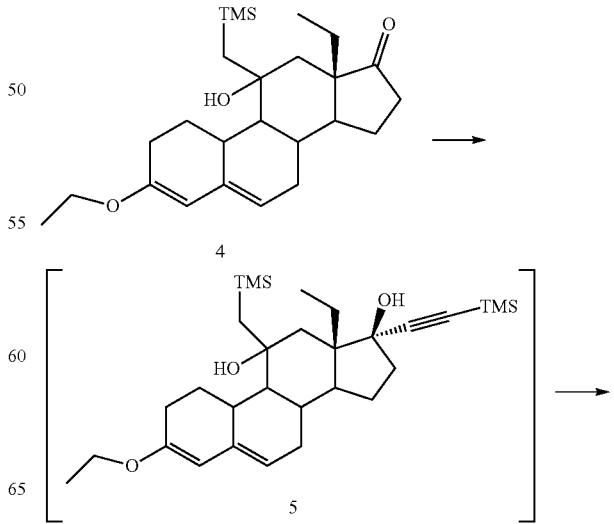

-continued

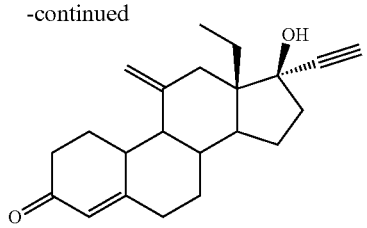

5

To a solution of hexillithium (65 mL) in heptane (100 mL) cooled at −5° C., a solution of trimethylsilyl acetylene (26 mL) in 100 ml of a mixture of THF/heptanes 1/3 was slowly added. The reaction mixture was stirred at −5° C. for 30 min, then a solution of compound 4 (10 g) in 100 mL of THF/heptanes 1:1 was added and the mixture stirred for 15 h further. Water (200 mL) was added to quench the excess of lithium reagent and the organic phase concentrated under vacuum. The residue (containing 90% of compound 5 and 10% of compound 4) was dissolved in 50 mL of methanol, 0.5 mL of HCl were added and stirred 1 h at 20° C., followed by addition of 3 mL of NaOH 50% and stirring for 1 h further. The solvent was evaporated under reduced pressure, the residue dissolved in 100 mL of DCM. It was washed first with a solution of glacial acetic acid 3% and then with a solution of NaHCO$_3$ 7%. The crude obtained was dissolved in 30 mL of acetone, concentrated to a volume of 12 mL and 12 mol of IPA were added with further reduction of the volume of 50%. The operation was repeated twice. The suspension was cooled in an ice bath and the solid filtered, washed with 4 mL of cold IPA and dried at 40° C. under vacuum, to yield 2.1 g of Etonogestrel.

Example 8. Synthesis of Compound 6 (Peterson Elimination/Deprotection)

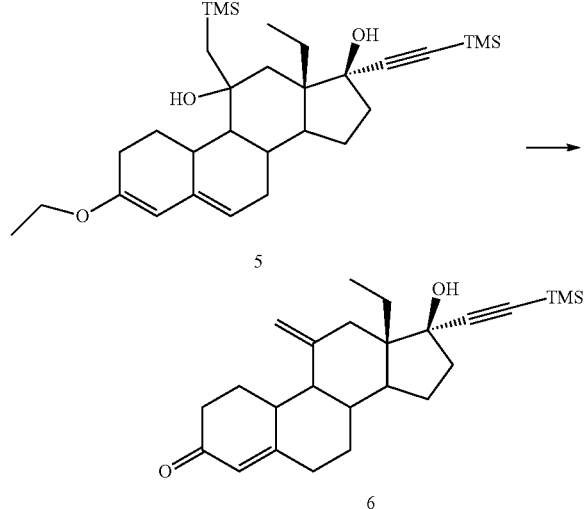

The residue obtained following Example 5 was dissolved in 20 mL of methanol and 2 mL of solution of HCl were added. The reaction mixture was stirred at 25° C. for 1 h, the solvent was then evaporated, 50 mL of water were added and the mixture extracted with 50 mL of EtOAc. The crude product was purified on silica gel with EtOAc/heptanes 1/9, affording pure compound 6 as a white solid.

Example 9. Synthesis of Compound 7 (TMS Deprotection)

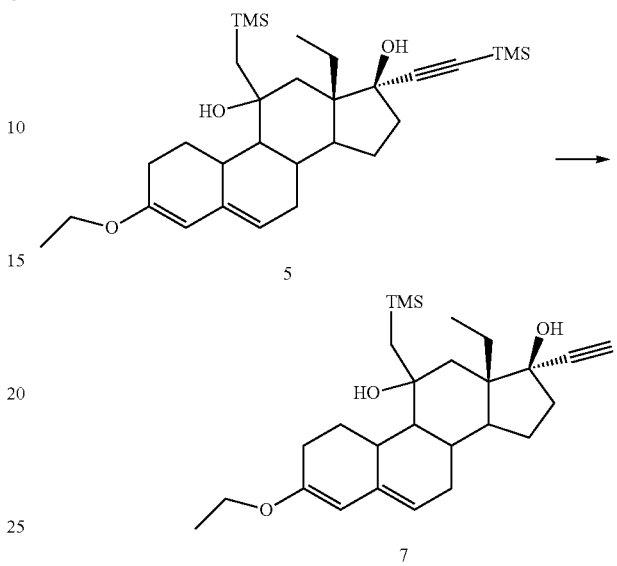

The residue obtained following Example 5 was dissolved in 20 mL of methanol and 2 mL of solution of NaOH 30% were added. The reaction mixture was stirred at 25° C. for 1 h, the solvent was then evaporated, 50 mL of water were added and the mixture extracted with 50 mL of EtOAc. The crude product was purified on silica gel with EtOAc/heptanes 1/9, affording pure compound 7 as an orange oil.

Example 10. Synthesis of Etonogestrel (TMS Deprotection)

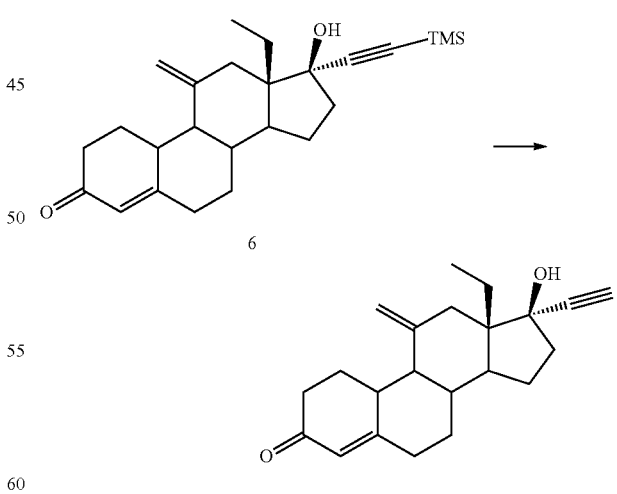

1 g of compound 6 was dissolved in 10 mL of acetone and then distilled up to a volume of 4 mL. 4 mL of IPA were added and concentrated up to a volume of 4 mL. The operation was repeated three times. The solution was then cooled at 0° C., filtered and washed with 2 mL of IPA. The solid was dried under vacuum to afford pure etonogestrel.

Example 11. Synthesis of Compound 8 (Ketone Protection)

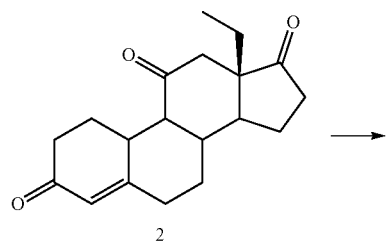

2

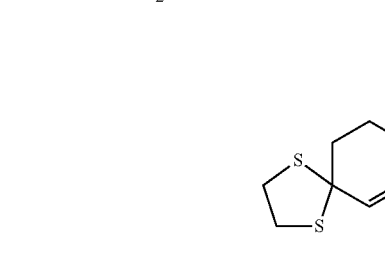

8

Compound 2 (28 g) was dissolved in DCM (280 mL), then 14 mL of 1,2-ethanedithiol and 1.4 g of pTsOH were added. The reaction mixture was refluxed for 5 h, 50 mL of DCM were distilling every hour (and adding fresh solvent). 140 mL of solution of NaHCO3 7% were added and the aqueous phase extracted with 50 mL of DCM. The combined organic phases were concentrated under vacuum to a final volume of 150 mL. 150 mL of methanol were added and concentrated under reduced pressure to a final volume of 100 mL. The obtained suspension was cooled in an ice bath for 1 h. The resulting solid was filtered, washed with 25 mL of cold methanol and dried under vacuum at 40° C., to yield 30 g of compound 8.

Example 12. Synthesis of Compound 9 (Peterson Olefination)

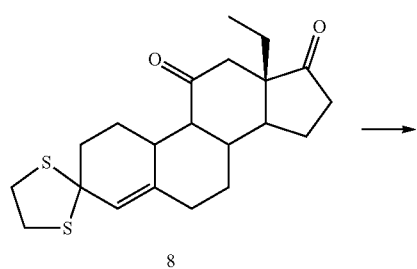

8

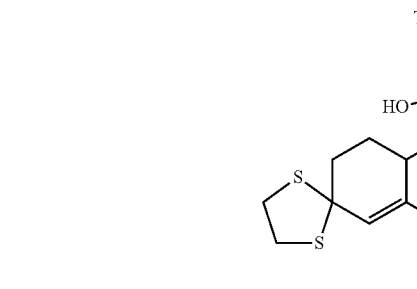

9

Compound 8 (20 g) was dissolved in THF (100 mL) and cooled at 0° C. Then 640 mL of trimethylsilyl methyl lithium were slowly added, keeping the temperature below 10° C. and the mixture was stirred for 1 h further after addition was complete. Then, 300 mL of solution of NaH$_4$Cl 12% were added, separated and the aqueous phase was extracted with 100 mL of EtOAc. The combined organic phases were concentrated to a volume of 100 mL and the suspension was cooled with an ice bath for 1 h. The resulting solid was filtered, washed with 30 mL of cold EtOAc and dried under vacuum at 40° C., to yield 11 g of compound 9 (43%).

Example 13. Synthesis of Compound 10 (Peterson Elimination)

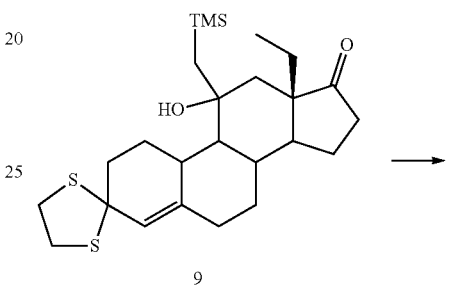

9

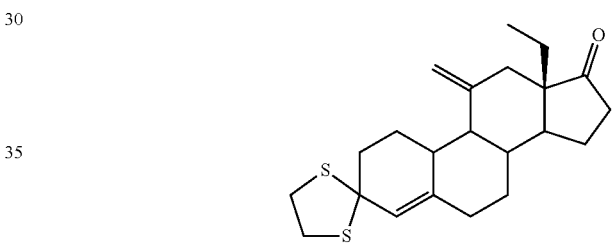

10

11 g of compound 10 were dissolved in 35 mL of methanol and 0.5 ml of HCl were added, the reaction mixture was stirred at 25° C. for 1 h. After adjusting the pH to 6 and adding TEA, the suspension was cooled in an ice bath. The resulting precipitate was filtered, washed with 10 mL of methanol and dried under vacuum at 40° C., affording 7.8 g of compound 11 (88%).

Example 14. Synthesis of Compound 11 (Ethynylation Reaction)

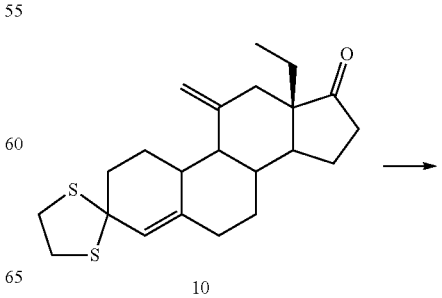

10

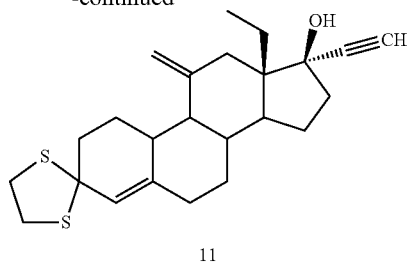

11

7.0 g of compound 10 were dissolved in 35 mL of THF, cooled down at 10° C. and 46 mL of LaCl$_3$*2LiCl were added, followed by slow addition of ethynylmagnesium chloride (159 mL) keeping the temperature below 15° C. After the addition was completed, the reaction mixture was heated for 2 h at 30° C. Then cooled down at 5° C. and 150 mL of a solution 10% HCl were added. The aqueous phase was extracted with 50 mL of EtOAc, and the combined organic phases were washed with brine. The solvent was evaporated under reduced pressure to a volume of 40 mL and 40 mL of heptane were added. It was concentrated to 40 mL and repeated twice. The obtained suspension was cooled in an ice bath for 1 h. The solid was filtered, washed with 10 mL of cold heptane and dried under vacuum at 40° C., to yield 5.8 g of compound 11 (77%).

Example 15. Synthesis of Etonogestrel (Ketone Deprotection)

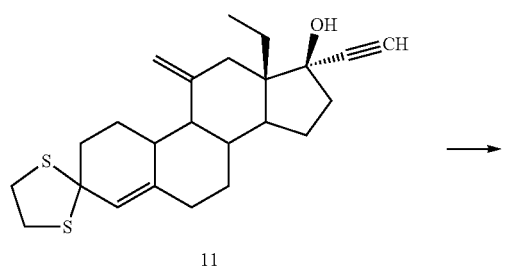

11

Thioacetal was removed using periodic acid, as described in example 8A in WO 2013/135744, or using SIBX as described in example 8C in WO 2013/135744.

Example 16. Synthesis of Compound 14 (Peterson Olefination)

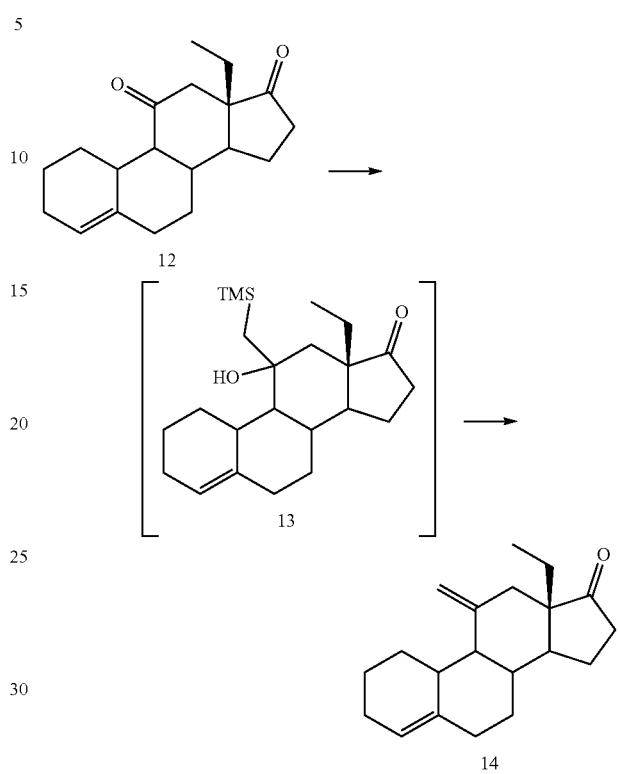

Compound 12 (10 g) was dissolved in THF (50 mL) and cooled at 0° C. Then, 330 mL of trimethylsilyl methyl lithium were slowly added, keeping the temperature below 10° C. and the mixture stirred for 1.5 h further after addition was complete. Then, 150 mL of solution of NaH$_4$Cl 12% were added, separated and the aqueous phase was extracted with 50 mL EtOAc. The combined organic phases were concentrated to a volume of 20 mL, and the suspension was cooled with an ice bath for 1 h. The resulting solid was filtered, dissolved in 20 mL of methanol, and 0.25 ml of HCl were added. The reaction mixture was stirred at 25° C. for 1.5 h. After adjusting the pH to 6 and adding TEA, the suspension was cooled in an ice bath. The precipitate was filtered, washed with 5 mL of methanol and dried under vacuum at 40° C., affording 7.6 g of compound 14 (76%).

Example 17. Synthesis of Desogestrel (Ethynylation Reaction)

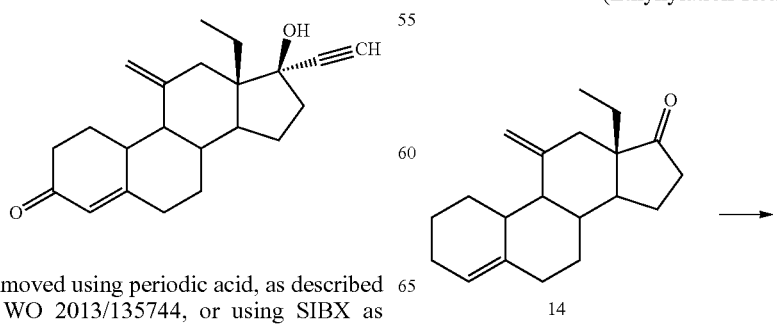

14

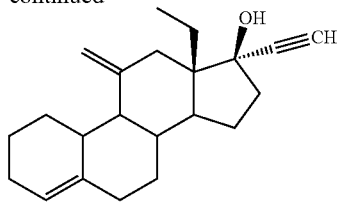

To a solution of hexillithium (3.0 g 2.3 M in hexane) in hexane (5 mL) cooled at −5° C., a solution of trimethylsilyl acetylene (1.32 g) in 6.8 mL of a mixture of THF/hexane 1/7 was slowly added. The reaction mixture was stirred at −5° C. for 30 min, then a solution of compound 14 (1.0 g) in 8 mL of hexane was added and the mixture stirred for 1 h at 0/5° C. Aqueous NaCl solution (8.5 mL) was added and the phases were separated. The organic phase was mixed with 5 mL of methanol, followed by addition of 1.5 mL of aqueous NaOH 30% and stirred for 4 h further. 10 mL of an aqueous solution of 3% Acetic acid was added. The phases were separated and the organic phase was washed with water (5.0 mL). The solvent was evaporated under reduced pressure and the residue dissolved in 1 mL of MeOH. The solvent was evaporated under reduced pressure and the residue dissolved in 2 mL of Hexane. The crude obtained was dissolved in 4 mL of hexane by heating at 60° C. The solution was cooled slowly in an ice bath and the resulting solid filtered, washed with 1 mL of cold hexane and dried at 40° C. under vacuum, to yield 0.89 g of Desogestrel (89%).

Example 18. Synthesis of Compound 15 (Methylation)

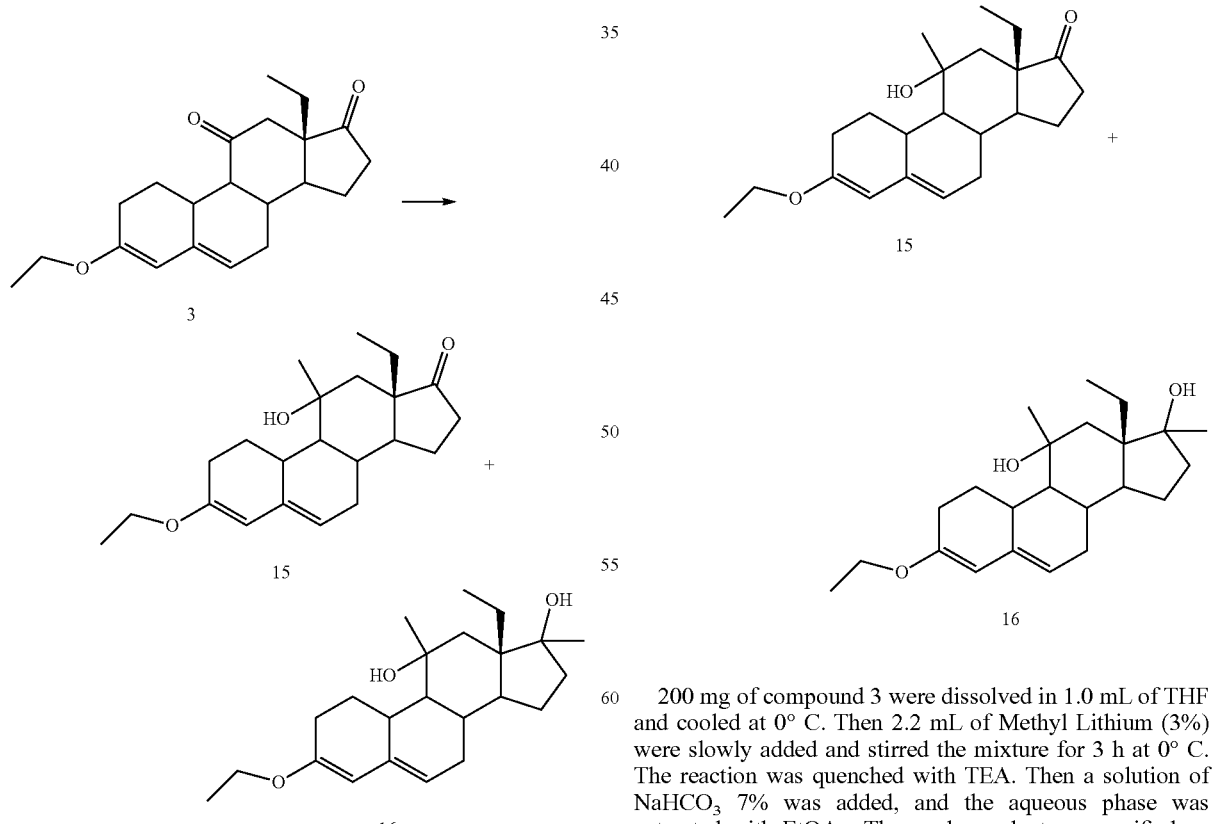

200 mg of compound 3 were dissolved in 1.0 mL of THF. Then 1.0 mL of methyl magnesium chloride (22%) were slowly added, heating the mixture at reflux for 3 h. The reaction was quenched with TEA. Then a solution of NaHCO$_3$ 7% was added and the aqueous phase was extracted with EtOAc. The crude product was purified on silica gel, affording compound 15 (75%) and the compound of di-methylation 16 (24%).

$^{13}$C NMR (100 MHz, CDCl$_3$): δ 8.3; 14.6; 18.5; 21.1; 29.2; 30.4; 33.8; 34.5; 35.5; 37.2; 43.2; 50.7; 51.8; 52.9; 62.3; 73.5; 100.1; 117.0; 137.7; 156.1; 219.2.

Example 19. Synthesis of Compound 15 (Methylation)

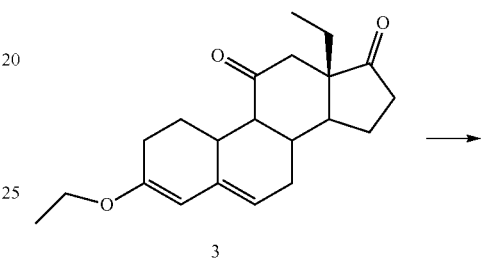

200 mg of compound 3 were dissolved in 1.0 mL of THF and cooled at 0° C. Then 2.2 mL of Methyl Lithium (3%) were slowly added and stirred the mixture for 3 h at 0° C. The reaction was quenched with TEA. Then a solution of NaHCO$_3$ 7% was added, and the aqueous phase was extracted with EtOAc. The crude product was purified on silica gel, affording compound 15 (76%) and the compound of di-methylation 16 (23%).

What is claimed is:

1. A compound of formula (Ic):

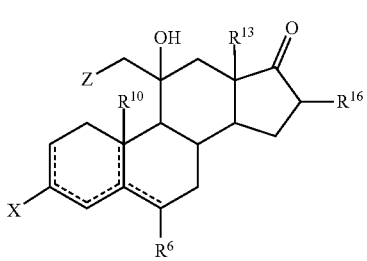

wherein:
- X represents H or it forms together with the carbon atom to which it is bonded a ketone protecting group;
- Z is selected from H and SiR'3 wherein each R' is independently selected from $C_1$-$C_6$ alkyl and $C_6$-$C_{10}$ aryl;
- $R^6$ is selected from H, $C_1$-$C_6$ alkyl and halogen;
- $R^{10}$ is selected from H, $C_1$-$C_6$ alkyl and halogen, or is absent when there is a double bond between $C_1$ and $C_{10}$;
- $R^{13}$ is selected from H and $C_1$-$C_6$ alkyl;
- $R^{16}$ is selected from H, $C_1$-$C_6$ alkyl and halogen; and
- ⚌ is a single or double bond;

said compound meeting one of the following conditions (a) to (c):

(a) wherein Z is SiR'3 wherein each R' is independently selected from $C_1$-$C_6$ alkyl and $C_6$-$C_{10}$ aryl;

(b) with the proviso that the compound of formula (Ic) does not represent:

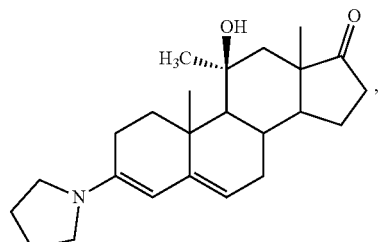

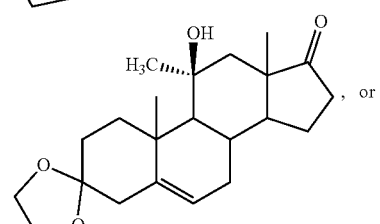

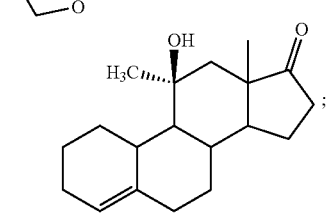

(c) which is selected from:
a compound of formula (Ia-1):

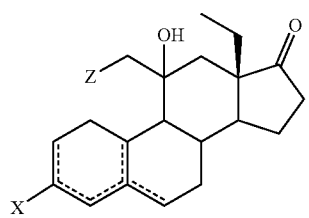

wherein:
- X forms together with the carbon atom to which it is bonded a ketone protecting group;
- Z is selected from H and SiR'3 wherein each R' is independently selected from $C_1$-$C_6$ alkyl and $C_6$-$C_{10}$ aryl; and
- ⚌ is a single or double bond;

and
a compound of formula (Ib-1):

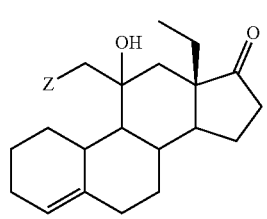

wherein:
Z is selected from H and SiR'3 wherein each R' is independently selected from $C_1$-$C_6$ alkyl and $C_6$-$C_{10}$ aryl.

2. A compound of formula (IVc):

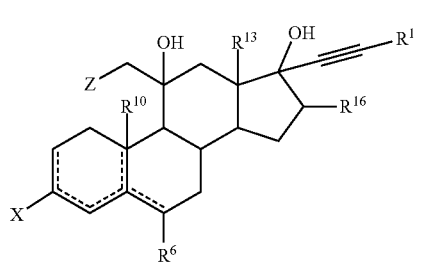

wherein
- X represents H or it forms together with the carbon atom to which it is bonded a ketone group or a ketone protecting group;
- Z is selected from H and SiR'3 wherein each R' is independently selected from $C_1$-$C_6$ alkyl and $C_6$-$C_{10}$ aryl;
- $R^1$ is selected from H and SiR''3, wherein each R'' is independently selected from $C_1$-$C_6$ alkyl, $C_6$-$C_{10}$ aryl and halogen;
- $R^6$ is selected from H, $C_1$-$C_6$ alkyl and halogen;
- $R^{10}$ is selected from H, $C_1$-$C_6$ alkyl and halogen, or is absent when there is a double bond between $C_1$ and $C_{10}$;

$R^{13}$ is selected from H and $C_1$-$C_6$ alkyl;
$R^{16}$ is selected from H, $C_1$-$C_6$ alkyl and halogen; and
═ is a single or double bond;
said compound meeting one of the following conditions (a) to (b):
(a) wherein $R^1$ is $SiR''_3$, wherein each R" is independently selected from $C_1$-$C_6$ alkyl, $C_6$-$C_{10}$ aryl and halogen;
(b) which is selected from:
a compound of formula (IVa-2):

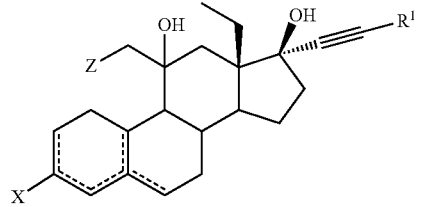

(IVa-2)

wherein
Z is $SiR'_3$ wherein each R' is independently selected from $C_1$-$C_6$ alkyl and $C_6$-$C_{10}$ aryl;
X forms together with the carbon atom to which it is bonded a ketone group or a ketone protecting group;
$R^1$ is selected from H and $SiR''_3$, wherein each R" is independently selected from $C_1$-$C_6$ alkyl, $C_6$-$C_{10}$ aryl and halogen; and
═ is a single or double bond;
and
a compound of formula (IVb-2):

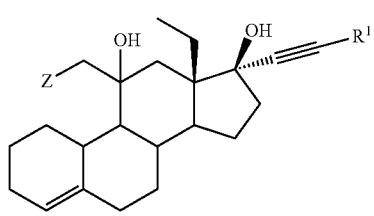

(IVb-2)

wherein
Z is selected from H and $SiR'_3$ wherein each R' is independently selected from $C_1$-$C_6$ alkyl and $C_6$-$C_{10}$ aryl; and
$R^1$ is selected from H and $SiR''_3$, wherein each R" is independently selected from $C_1$-$C_6$ alkyl, $C_6$-$C_{10}$ aryl and halogen.

3. The compound according to claim 1, which is selected from the group consisting of:

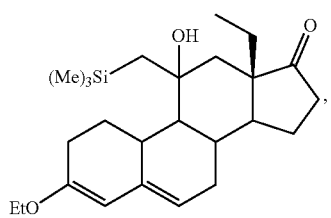

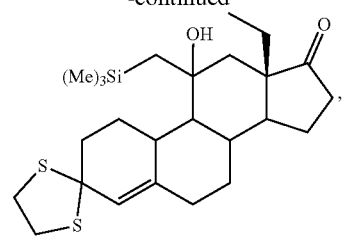

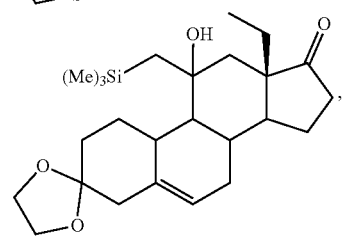

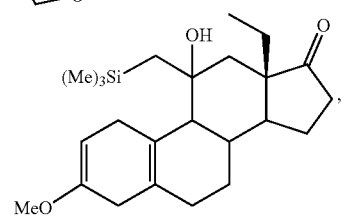

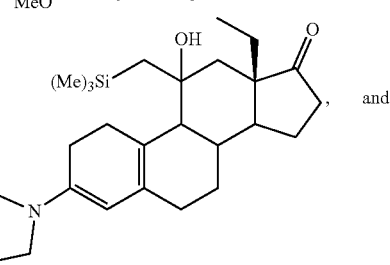

and

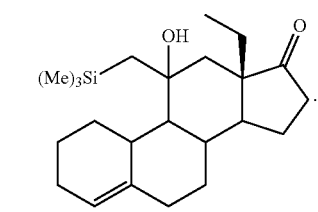

4. The compound according to claim 2, which is selected from the group consisting of:

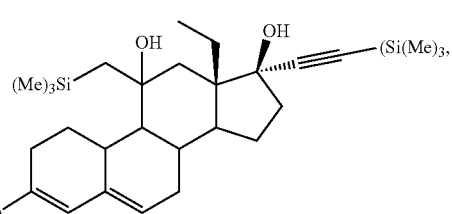

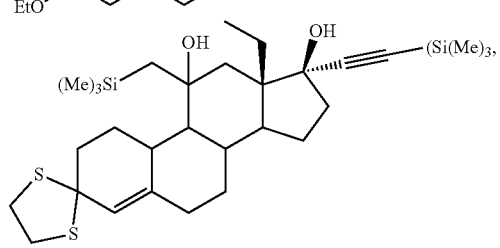

53
-continued
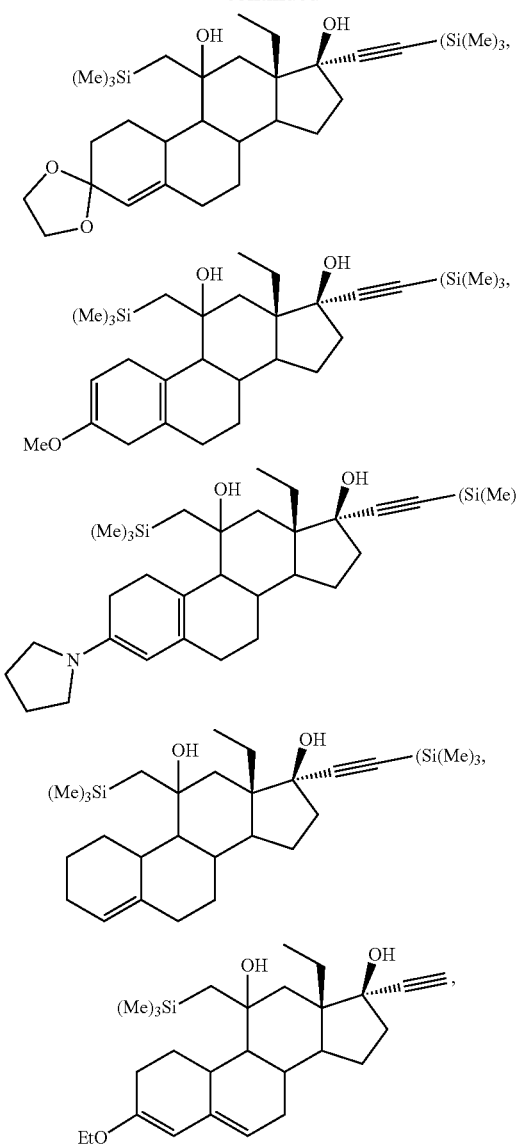
54
-continued
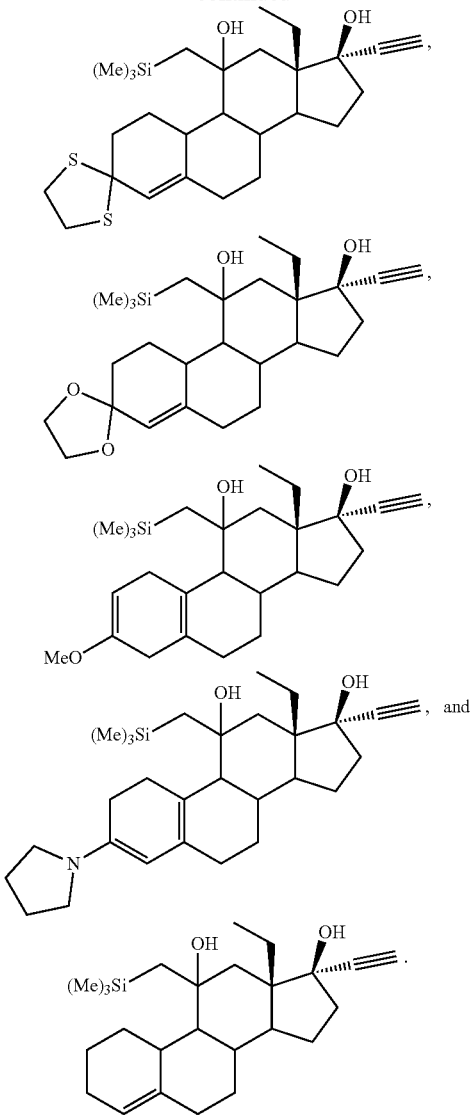
* * * * *